(12) United States Patent
Carpenter et al.

(10) Patent No.: US 8,005,188 B2
(45) Date of Patent: Aug. 23, 2011

(54) TEST-SENSOR PRODUCTION MONITORING USING XRF SPECTROMETRY

(75) Inventors: Scott E. Carpenter, Pendleton, IN (US); Theresa A. Rey, South Bend, IN (US); Huan-Ping Wu, Granger, IN (US)

(73) Assignee: Bayer Healthcare LLC, Tarrytown, NY (US)

( * ) Notice: Subject to any disclaimer, the term of this patent is extended or adjusted under 35 U.S.C. 154(b) by 348 days.

(21) Appl. No.: 12/225,832

(22) PCT Filed: Apr. 5, 2007

(86) PCT No.: PCT/US2007/008387
§ 371 (c)(1),
(2), (4) Date: Sep. 30, 2008

(87) PCT Pub. No.: WO2007/120552
PCT Pub. Date: Oct. 25, 2007

(65) Prior Publication Data
US 2009/0310743 A1    Dec. 17, 2009

Related U.S. Application Data

(60) Provisional application No. 60/790,984, filed on Apr. 11, 2006, provisional application No. 60/836,034, filed on Aug. 7, 2006.

(51) Int. Cl.
*G01N 23/223* (2006.01)
*C12Q 1/00* (2006.01)
(52) U.S. Cl. .............................................. 378/45; 435/4
(58) Field of Classification Search .................. None
See application file for complete search history.

(56) References Cited

U.S. PATENT DOCUMENTS 6,531,040 B2   3/2003  Musho et al. ................. 204/401
2006/0113187 A1*  6/2006  Deng et al. ............... 204/403.01

FOREIGN PATENT DOCUMENTS
WO    WO 2005/040404 A1   5/2005

OTHER PUBLICATIONS

Heider et al. Electrochemical Platinization of Reticulated Vitreous Carbon Electrodes to Increase Biosensor Response; Analytical Chemistry, vol. 62 (1990) pp. 1106-1110.*
Griffith et al. Probing Enzyme Polymer Sensors Using X-Ray Photoelectron Spectroscopy: Determination of Glucose Oxidase in Electropolymerized Films; Biosensors and Bioelectronics, vol. 11, No. 6/7 (1996) pp. 625-631.*
Nazaruk et al. Enzymatic Electrodes Nanostructured With Functionalized Carbon Nanotubes for Biofuel Cell Applications; Analytical and Bioanalytical Chemistry, vol. 398 (2010) pp. 1651-1660.*
Imre Szalóki, János Osán and René E. Van Grieken, *X-Ray Spectrometry*, Anal. Chem. 2004, vol. 76, pp. 3445-3470.
P. Hahn-Weinheimer, A. Hirner and K. Weber-Diefenbach, *Grundlagen and praktische Anwendung der Röntgenfluoreszenzanalyse (RFA)*, 1984, Friedr. Vieweg & Sohn, Braunschweit.
Written Opinion corresponding to International Patent Application No. PCT/US2007/008387, European Patent Office, dated Oct. 31, 2007, 4 pages.
International Search Report corresponding to International Patent Application No. PCT/US2007/008387, European Patent Office, dated Oct. 31, 2007, 5 pages.

* cited by examiner

*Primary Examiner* — Rebecca Prouty
*Assistant Examiner* — Paul Martin
(74) *Attorney, Agent, or Firm* — Nixon Peabody LLP

(57) ABSTRACT

A method for monitoring test sensors comprising the steps of, providing a test sensor comprising a reagent including an enzyme and a metal mediator; monitoring the amount of metal in the mediator of the reagent using X-ray fluorescence spectrometry and determining from the amount of metal in the mediator an amount of the reagent on the test sensor.

23 Claims, 14 Drawing Sheets

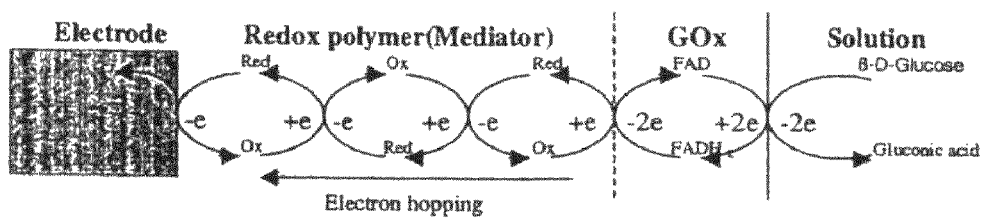
Figure 4. Illustration of redox polymer mediated biosensing process.

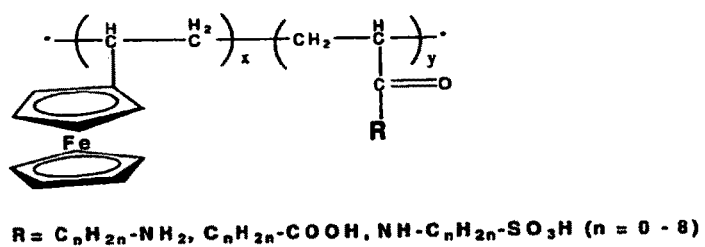
$R = C_nH_{2n}\text{-}NH_2, C_nH_{2n}\text{-}COOH, NH\text{-}C_nH_{2n}\text{-}SO_3H \ (n = 0 - 8)$
Figure 5. Structure of water-soluble and cross-linkable ferrocenyl redox polymer.

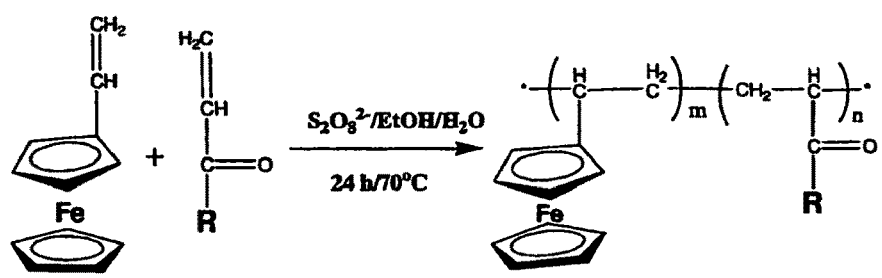
R= $C_nH_{2n}$-$NH_2$, $C_nH_{2n}$-COOH, NH-$C_nH_{2n}$-$SO_3H$ (n = 0 - 8)
Figure 6. Polymerization mechanism of the redox polymer

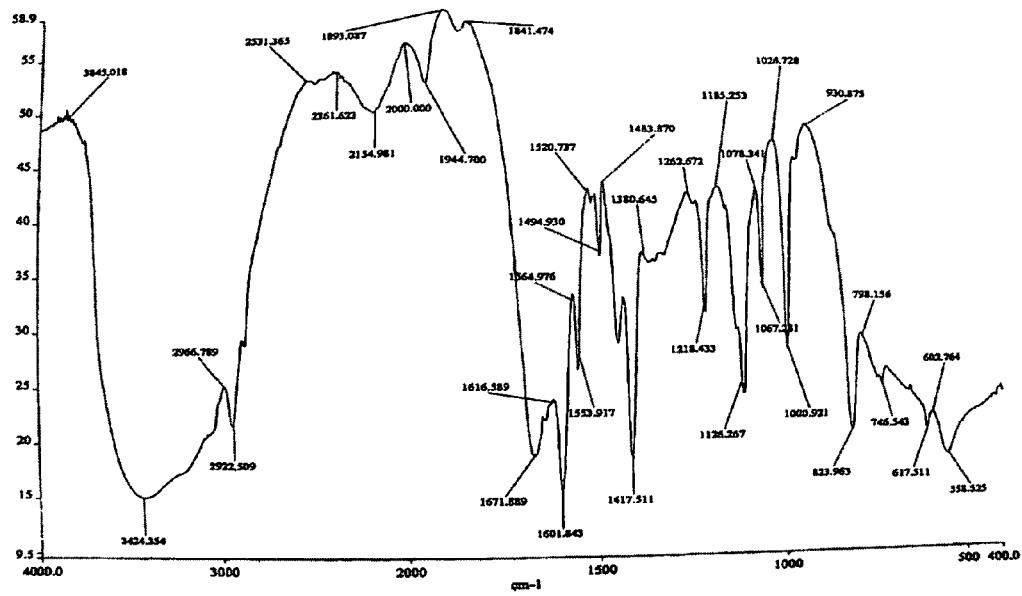
FIGURE 7. FT-IR Spectrum of PAA-VFc and PAAS-VFc redox polymer
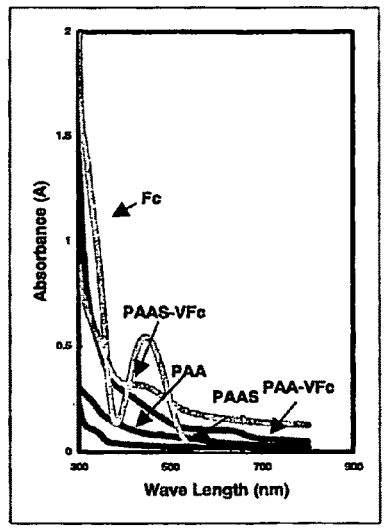
FIGURE 8. UV-visible spectra of Fc, PAA PAAS and their VFc co-polymers.

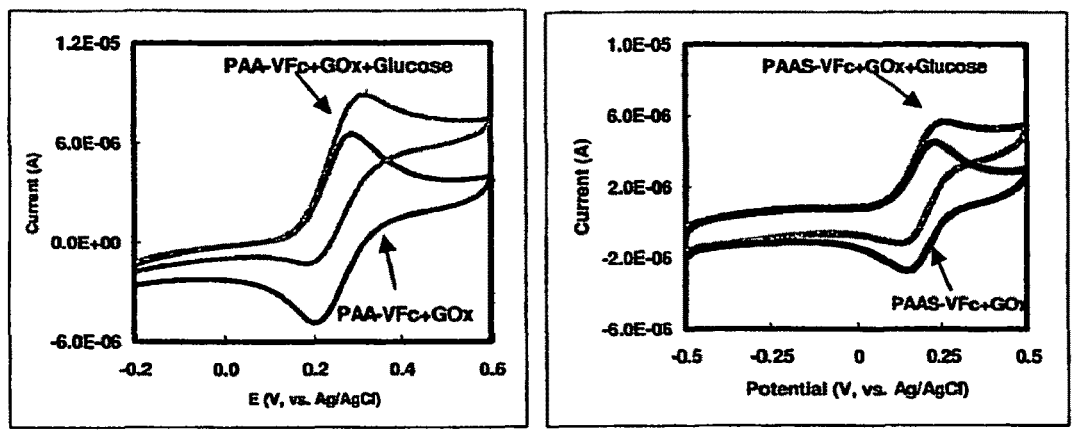
Figure 9. Cyclic voltammograms of redox polymers in various systems.
Phosphate-buffered saline, potential scan rate = 100 mV/s

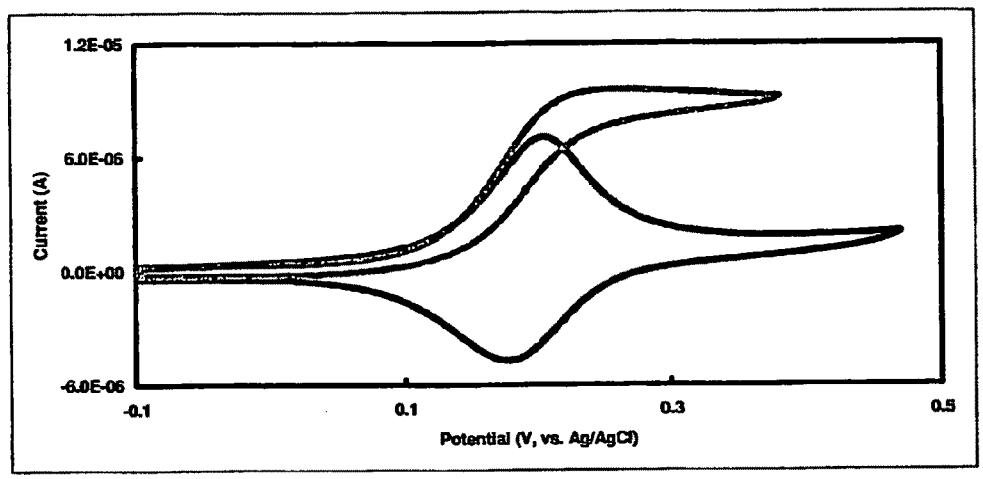
Figure 10. Cyclic voltammogram of cross-linked PAA-VFc-GOx-BSA film
on gold electrode.
PBS, potential scan rate 50 mV/s.

TEST-SENSOR PRODUCTION MONITORING USING XRF SPECTROMETRY

CROSS-REFERENCE TO RELATED APPLICATIONS

This application claims priority to Application Nos. 60/790,984 filed on Apr. 11, 2006 and 60/836,034 filed on Aug. 7, 2006, which are incorporated by reference in their entirety.

The present invention relates to sensors, in particular sensors for determining the presence of analytes in a test sample. The invention also relates to nanoparticulate membranes. The invention further relates to water-soluble redox polymers and processes for preparing the polymers.

BACKGROUND OF THE INVENTION

In recent years, polymeric materials have gained widespread theoretical interest and practical use in many fields [G. Harsanyi. Materials Chemistry and Physics Vol. 43, Issue 3, 1996, 199]. Conducting polymers in particular have found increasing use in the field of biosensing, where conducting polymers provide a unique function as an interface between smart sensors and intelligent molecular receptors. Of all the known conducting polymers, such as ionically conducting polymers, charge transfer polymers and conjugated conducting polymers, redox polymers are by far most widely used in biosensing applications.

Glucose sensing, an area in biosensing which has been undergoing significant research in recent years, relies on electron mediation of enzymatic oxidation of glucose to gluconic acid by glucose oxidase is required. The electron mediating function of redox polymers has been widely studied and applied to many amperometric glucose biosensors.

In its natural enzymatic reaction, co-enzyme flavin adenine dinucleotide (FAD) is an electron carrier present in glucose oxidase is reduced to $FADH_2$ (reduced form of FAD) and oxidized back to FAD by molecular oxygen. $O_2$ is then reduced to $H_2O_2$. This cyclic oxidation and reduction enables FAD to act as an electron acceptor. Since neither glucose nor gluconic acid is electro-active within the working potential window from −0.5 to 1.0 V, either the increase in $H_2O_2$ concentration or the decrease in $O_2$ concentration is being measured to quantify the glucose concentration.

However, the accuracy of measurements based on the measurement of $H_2O_2$ and $O_2$ is compromised because firstly, the partial pressure of atmospheric $O_2$ affects amperometric response, and secondly, the quantitative measurement of $O_2$ at high glucose concentration is difficult because $O_2$ is used up as the sensing proceeds. The detection of $H_2O_2$ by its oxidation at a platinum electrode requires a working potential of 0.5 to 0.6 V (vs. Ag/AgCl), and thus is subjected to interferences of electro-active species in blood, such as ascorbic acid and uric acid which are electrochemically active at this potential.

To circumvent the above-mentioned problems associated with glucose monitoring involving $O_2$ or $H_2O_2$, redox-active mediators have been proposed as artificial electron acceptors in place of oxygen molecules for $FADH_2$.

A successful mediator should, in principle, meet three requirements: (1) fast electron-exchange rate with enzyme and electrode, (2) stable attachment to the electrode and (3) processable in aqueous medium.

For this reason, two groups of mediators were extensively investigated, namely, transition metal complexes and ferrocenyl materials. In recent years, many groups have focused their attention on the synthesis and biosensing applications of ferrocenyl materials, both monomeric and polymeric. For example, polyferrocenyl compounds have been used as redox indicators in molecular recognition [J. E. Kinston, et al, J. Chem. Soc., Dalton. Trans (1999) 251.], as mediators in biosensors [S. Kolde, et al, J. Electroanal. Chem., 468 (1999) 193.] and as coating to modified electrode surface [S, Niate, et al, Chem. Commun., (2000) 417.]. However, most of the known ferrocenyl materials are only soluble in non-polar media, only few ferrocenyl and polyferrocenyl materials are water-soluble [O. Hatozaki, et al, J. Phys. Chem., 199 (1996) 8448.]. Water-soluble ferrocenyl materials are of particular interest as redox mediators in biosensing. By co-polymerizing alkene substituted ferrocenes, such as vinylferrocene, with an appropriate water-soluble polymer, it is possible to prepare ferrocenyl materials that are readily soluble in water. But it has been shown that the free radical in initiated polymerization of vinylferrocene is unusual [A. J. Tinker, et al, J. Polym Sci., Polym. Chem. Ed., 13 (1975) 2133; M. H. George, et al, J. Polym Sci., Polym. Chem. Ed., 14 (1975) 475.]. Co-polymerization of vinylferrocene is known to be difficult because the ferrocenium is a radical scavenger in the polymerization system, resulting in that the reaction does not obey normal radical polymerization kinetics. Termination of the polymerization reaction occurs by an intramolecular electron transfer from a ferrocene nucleus to the growing chain radical. This leads to the deactivation of the polymer chain and a polymer which contains a high spin Fe(III) species.

Polyacrylamide has been widely used as support matrix in enzyme immobilization and biosensing because of its good chemical and mechanical stability and its inertness to microbial degradation [I, Willner, et al, J. Am. Chem. Soc., 112 (1990) 6438.]. However, attempts of co-polymerization of vinylferrocene and acrylamide and its derivatives were not successful [H. Bu, et al, Anal. Chem., 67 (1995) 4071 and references therein.]. Instead, to by-pass the inefficient co-polymerization of vinylferrocene, chemical grafting procedures were proposed in preparing ferrocenyl materials [S. Koide, et al, J. Electroanal. Chem., 468 (1999) 193; J. Hodak, et al, Langmuir, 13 (1997) 2708; K Salmon, et al, J. Organomet. Chem., 637-639 (2001) 595.]. In two recent reports [N. Kuramoto, et al, Polymer 39 (1998) 669; H. Ahmad, et al, Colloids and Surfaces, 186 (2001) 221], vinylferrocene copolymers were synthesized, but minute loading of ferrocene and lack of cross-linkable groups in these polymers restrict their use in biosensors.

Commercially available biosensors include those manufactured by Therasense Inc. (cf., for example U.S. Pat. No. 6,338,790), Inverness Medical Technology (cf., for example U.S. Pat. No. 6,241,862) and Matsushita Electric (cf., for example, U.S. Pat. No. 6,547,954).

Therefore, there remains the need for vinylferrocene-based polymeric mediators having superior performance characteristics. Consequently, it is a goal of the present invention to develop new methods of synthesis for new vinylferrocene-based polymeric mediators. it is also a goal of this invention to provide biosensors with enhanced performance, and which would impose minimal inconvenience to the end user of the biosensor as much as possible.

These goals are solved by the various aspects of the present invention, namely the sensors, membranes, polymers, and processes as defined in the respective independent claims.

SUMMARY OF THE INVENTION

In one aspect, the invention provides a sensor for determining the presence of an analyte in a test sample, said sensor comprising a nanoparticulate membrane comprising nanoparticles of at least one inorganic oxide of an element selected from Group IA, IIA, IIIA, IVA, IB, IIB, IIIB, IVAB, VB, VIIB, VIIB or VIIIB of the Periodic Table, and wherein an oxidoreductase enzyme and electrochemical activator are diffusibly dispersed in said nanoparticulate membrane.

In yet another aspect, the invention provides an electrically non-conductive, nanoparticulate membrane comprising nanoparticles of at least one inorganic oxide of an element selected from Group IA, IIA, IIIA, IVA, IB, IIB, IIIB, IVAB, VB, VIIB, VIIB or VIIIB of the Periodic Table, and wherein an oxidoreductase enzyme and electrochemical activator are diffusibly dispersed in said nanoparticulate membrane.

In a further aspect the invention provides a process for producing an electrically non-conductive, nanoparticulate membrane comprising mixing an electrochemical redox mediator with an oxidoreductase enzyme and nanoparticles of an oxide of an element selected from Group IA, IIA, IIIA, IVA, IB, IIB, IIIB, IVAB, VB, VIIB, VIIB or VIIIB to form a nanocomposite ink; and applying said nanocomposite ink onto a substrate.

In yet another aspect, the invention provides a water soluble redox polymer comprising:
  a first monomer unit comprising a polymerisable ferrocene derivative; and
  a second monomer unit comprising an acrylic acid derivative having a (terminal) primary acid or base acid or base functional group capable of acquiring a net charge.

In one embodiment, the acrylic acid derivative in this new water soluble redox polymer is represented by the general formula (I)

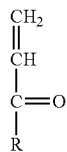

wherein R is selected from the group consisting of $C_nH_{2n}$—$NH_2$, $C_nH_{2n}$—COOH, NH—$C_nH_{2n}$—$PO_3H$ and NH—$C_nH_2$,—$SO_3H$, wherein the alkyl chain can be optionally substituted, and wherein n is an integer from 0 to 12.

In yet another aspect, the invention provides a process for preparing a water soluble, redox polymer, said process comprising:
  polymerizing a first monomer unit comprising a polymerisable ferrocene derivative with a second monomer unit comprising an acrylic acid derivative having an acid or base functional group capable of acquiring a net charge, wherein said polymerization is carried out in an aqueous alcoholic medium.

BRIEF DESCRIPTION OF THE DRAWINGS

The invention will be better understood with reference to the detailed description when considered in conjunction with the non-limiting examples and the drawings, in which:

FIG. 4 shows a schematic diagram of the coupling redox reaction which takes places in a redox polymer mediated biosensor.

FIG. 5 illustrates a structure of the basic unit of a water-soluble and cross-linkable polymer of the present invention. The figure shows a repeating unit found in a copolymer of vinylferrocene and an acrylic acid derivative.

FIG. 6 depicts the general reaction equation in the co-polymerization reaction of vinyl ferrocene and an acrylic acid derivative.

FIG. 7 shows a Fourier Transform Infra Red (FT-IR) spectrum of the redox polymers PAA-VFc and PAAS-VFc produced according to a process of the invention.

FIG. 8 shows an Ultra Violet (UV)-visible spectra of Fc, PM, PAAS and the co-polymers obtained from copolymerization with VFc.

FIG. 9 shows cyclic voltammograms of redox polymers in various systems. Phosphate-buffered saline was used, and the potential scan rate applied in obtaining the voltammograms was 100 mV/s.

FIG. 10 shows another cyclic voltammogram of a redox polymer PM-VFc that is cross-linked with glucose oxidase-bovine serum albumin (GOx-BSA) film on gold electrode. Phosphate-buffered saline was used, and the potential scan rate applied in obtaining the voltammograms was 50 mV/s.

DETAILED DESCRIPTION

Figure 1:
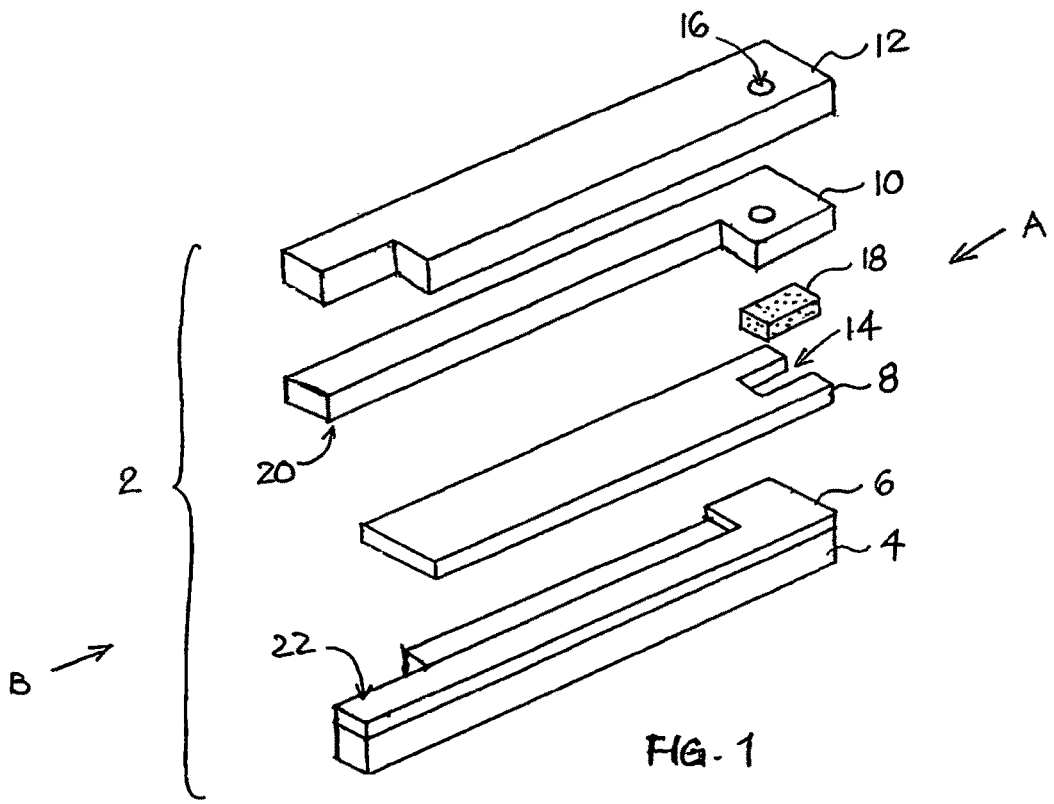
FIG. 1 is an exploded isometric drawing of a biosensor according to an embodiment of the invention.
Figure 3:
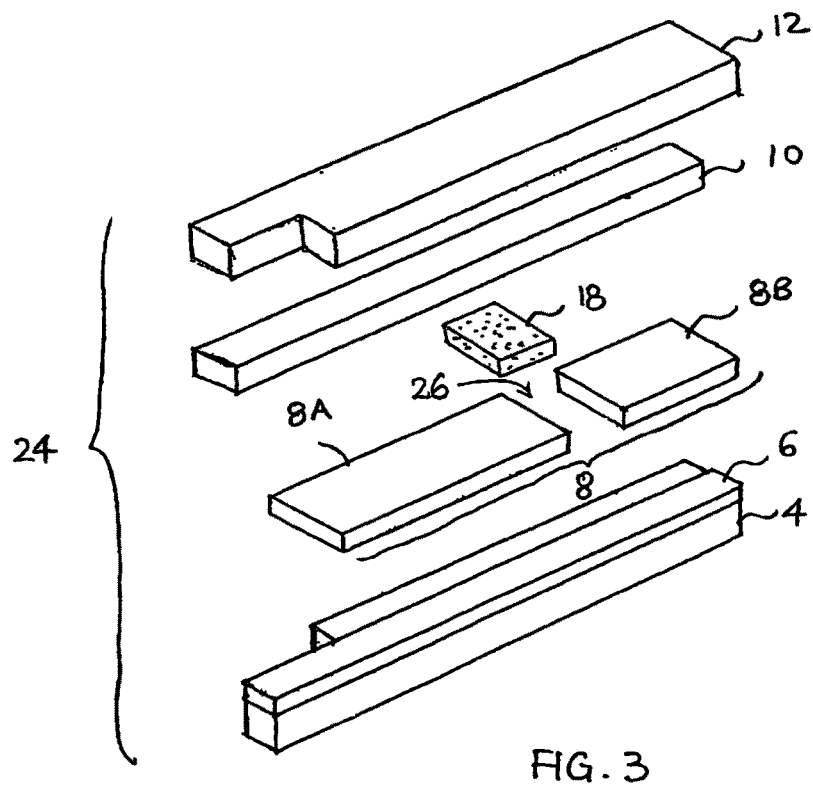
FIG. 3 is an exploded isometric drawing of a biosensor according to another embodiment of the invention.

In one aspect, the present invention is based on the finding that water-soluble and cross-linkable redox polymers can be readily prepared in a mixture of ethanol and water with a persulfate salt as radical initiator. This method of preparation allowed problems faced earlier such as the unfavorable energetics of copolymerization reactions involving ferrocene molecules to be overcome. Tests showed that the molecular weight of vinylferrocene-co-acrylamide copolymers obtained from this method was in the range of 2000 to 4000 Daltons, corresponding to about 400 monomeric units with 3-14% ferrocene loading. Such a level of ferrocene loading was previously achievable using free radical polymerization techniques (see for example N. Kuramoto et al). By overcoming this limitation, the present invention has given rise to new polymers with useful properties for biosensing applications and other methods of electrochemical detection of analytes.

The ferrocene centers in redox polymers of the invention are able to provide localized electroactivity and thus the ability to engage in redox reactions without bringing about a reorganization of intra molecular bonds in the polymer. Furthermore, redox polymers of the invention comprise side chains with functional groups that facilitate cross-linking with other molecules with suitable functional groups. This allows the polymer to be attached to a wide variety of molecules as well. Combining these two characteristics, these polymers are well adapted for use in applications requiring electron mediation, such as enzyme electrodes used in biosensors and biofuel cells, as well as enzymatic synthesis carried out in electroenzyme reactors.

In another aspect, glucose sensors according to the present invention incorporate sensing elements that are capable of accurately measuring the concentration of glucose found in very small quantities of fluid, so that test samples of less than 1 μL, or preferably about 0.2 μL to 0.3 μL, is needed. Test samples typically include animal biological samples such as biological fluids (e.g. blood samples, sweat samples, urine samples); faecal samples, and flesh samples containing adipose tissue or subcutaneous fat. Other samples that can be analyzed using the present sensor include reagents utilized in scientific experiments, or food with glucose content and fermentation broths found in the wine or beer production industries. Test samples can also include microbiological culture mediums (e.g. a growth medium for high density fermentation of $E.\ coli$, yeast or other host organisms, typically used for recombinant production of polypeptides).

Due to the small volume of test sample that is required for performing a diagnostic test, minimal inconvenience is imposed on the end user. For example, for diabetics that require continuous blood glucose assessment, withdrawal of a blood sample at a sub-microliter level would Impose minimal pain and disturbance to the patient.

In general, a sensor of the present invention makes use of an nanoparticulate membrane which is described herein in detail. In addition to the fact that it is suitable for testing of blood sample at a sub-microliter level, such a membrane has the advantage that is can be produced at low cost, and is stable even under prolonged periods of storage.

The membrane can incorporate an electrochemical activator and a substrate-specific enzyme, both diffusibly dispersed in a membrane deposited onto an electrode of the sensor where glucose is oxidized. The term "electrochemical activator" as used herein refers to any compound that is capable of activating the enzyme that transfers electrons between glucose and the working (detection) electrode of the sensor. The electrochemical activator can be a polymeric redox mediator. Alternatively, monomeric electrochemical activators can also be used, such as water soluble ferrocene derivatives, osmium-bipyridine complexes, ruthenium complexes (e.g. pentaamine pyridine ruthenium and $Ru(NH_3)_6^{3+}$) as well as hexacyanoferrate and hexacyanoruthenate. In some embodiments of the invention, the electrochemical activator contains redox-active metal ions. Examples of such metal ions are silver, gold, copper, nickel, iron, cobalt, osmium or ruthenium ions or mixtures thereof.

In general, suitable polymeric redox mediators to be incorporated into the nanoparticulate membrane of the invention should have a chemical structure which prevents or substantially reduces the diffusional loss of the redox species during the period of time that the sample is being analyzed. The diffusional loss of the redox mediator can be reduced by rendering the polymeric redox mediator non-releasable from the working electrode in the sensor. This can be achieved by binding or immobilizing the redox mediator, for example, by covalently attaching or biconjugation of the redox mediator to a polymer on an electrode. Alternatively, the redox mediator can be immobilized by providing a binder having counter-charge species or species having high affinity for the redox mediator. In one embodiment of the invention, one type of non-releasable polymeric redox mediator comprises a redox species covalently attached to a polymeric compound. Such redox polymers typically are transition metal compounds, wherein a redox-active transition metal-based pendant group is covalently bound to a suitable polymer backbone, which on its own may or may not be electroactive itself. Examples of this type are poly(vinyl ferrocene) and poly(vinyl ferrocene co-acrylamide). Alternatively, the polymeric redox mediator may comprise an ionically-bound redox species. Typically, these mediators include a charged polymer coupled to an oppositely charged redox species. Examples of this type Include a negatively charged polymer such as Nafion® (Dupont) coupled to a positively charged redox species such as an osmium or ruthenium polypyridyl cation or vice versa a positively charged polymer such as poly(1-vinyl imidazole) coupled to a negatively charged redox species such as ferricyanide or ferrocyanide. Furthermore, the redox species can also be coordinatively bound to the polymer. For example, the redox mediator may be formed by coordination of an osmium or cobalt 2,2'-bipyridyl complex to poly(1-vinyl imidazole) or poly (4-vinyl pyridine). Another example is poly(4-vinyl pyridine co-acrylamide) coordinated with an osmium 4,4'-dimethyl-2,2'-bipyridyl complex. Useful redox mediators as well as methods for their synthesis are described in U.S. Pat. Nos. 5,264,104; 5,356,786; 5,262,035; 5320,725; 6,336,790; 6,551,494; and 6,576,101.

In a further embodiment of the invention, the electrochemical activator is selected from the novel class of redox polymers that is described in detail later herein. Briefly, this novel class of redox polymers comprises poly(vinyl ferrocene), poly(vinyl ferrocene)-m-acrylamide, poly(vinyl ferrocene)-co-acrylic acid, and poly(vinyl ferrocene)-co-acrylamido-$(CH_2)_n$-sulfonic acid, and poly(vinyl ferrocene)-co-acrylamido-$(CH_2)_n$-phosphonic acid, wherein n is an integer from 0 to 12, preferably 0 to 8.

The membrane of the invention can also incorporate a redox polymer that is cross-linked with a protein such as an enzyme or antigen and immobilized on an electrode surface.

One embodiment of the sensor, comprises a chamber for holding the test sample, whereby the chamber is bounded at least between a working area on a working electrode and a working area on a reference electrode. Also in this embodiment, the oxidoreductase enzyme and water soluble redox polymer is coated on the working area of the working electrode.

Figure 2A:
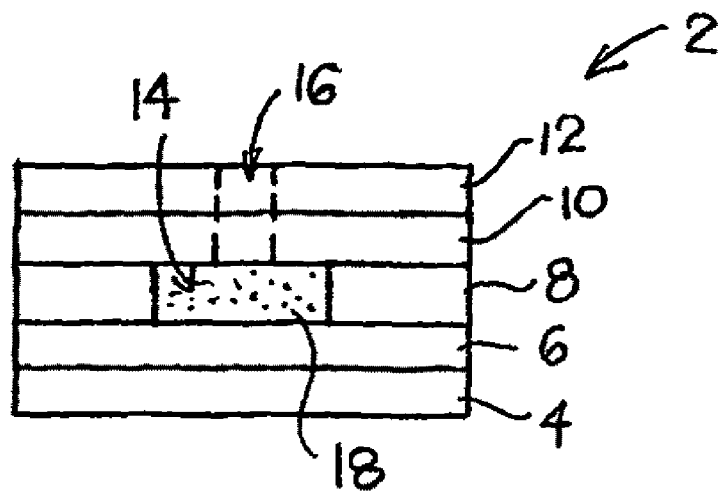
FIG. 2A is a drawing showing an end view of the biosensor in FIG. 1, as seen in the direction of an arrow A in FIG. 1.
Figure 2B:
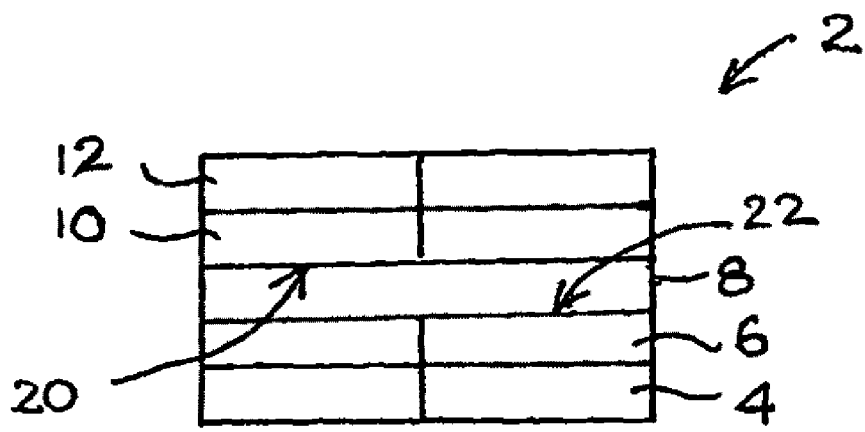
FIG. 2B is a drawing showing another end view of the biosensor in FIG. 1, as seen in the direction of an arrow B in FIG. 1.
Figure 11:
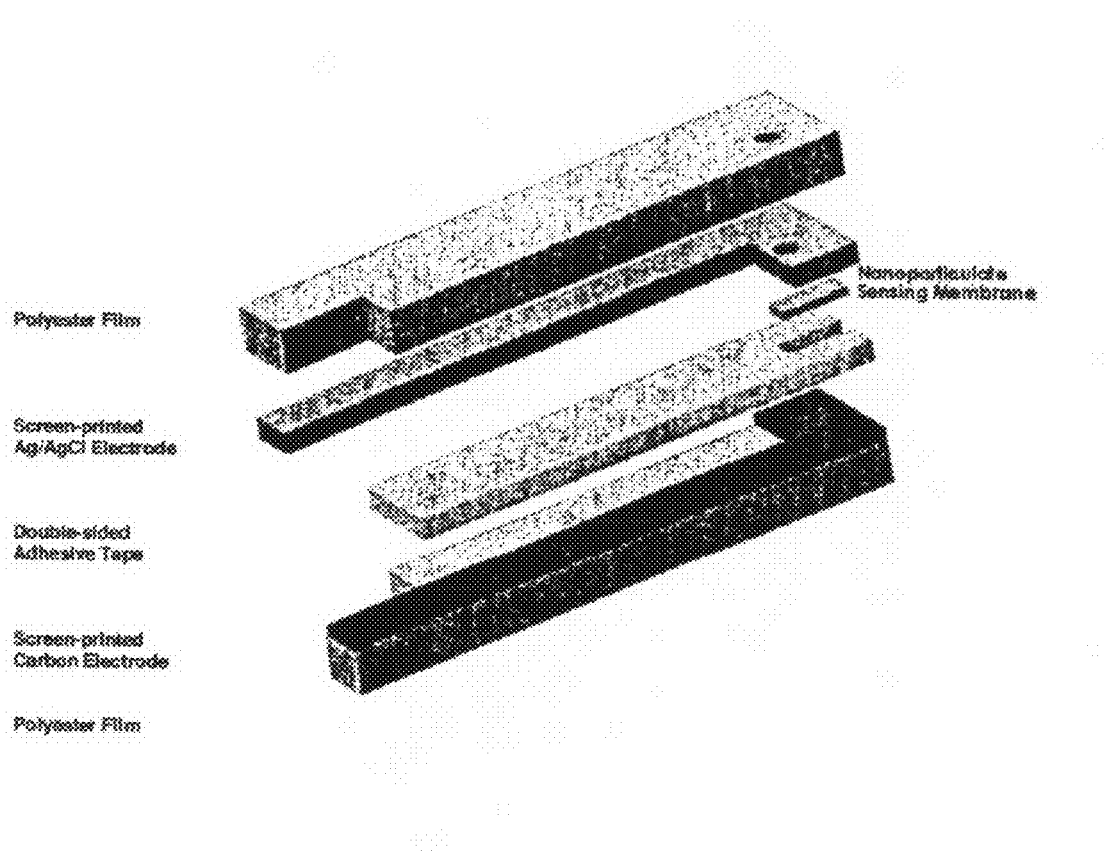
FIG. 11 shows an exploded view of a disposable glucose biosensor used in this work.

Referring to the figures, a sensor of the invention is described as follows. FIG. 1 shows an exploded isometric view of a tip-filling biosensor 2 according to an embodiment of the present invention. The biosensor 2 includes a stack made up of several layers. The stack includes, from bottom to top according to FIGS. 1 and 2, a substrate layer 4, a working electrode 6, a spacer 8, a counter electrode 10, and a top layer 12. The spacer 8 spaces apart the working electrode 6 and counter electrode 10 to thereby electrically Insulate them. A recess 14, formed between two legs of a bi-furcated end of the spacer 8, defines a sample chamber 14 (see FIG. 2A) between the working electrode 6 and the counter electrode 10. In this manner, the sample chamber 14 is bounded or defined on the top and bottom by opposite facing surfaces of the counter electrode 10 and the working electrode 6 respectively; and on the sides by sidewalls the spacer 8. One side of the sample chamber 14 is exposed as shown in FIG. 2. This surface of the working electrode 6 is referred to as a working surface. A sensing chemistry materials carrier, such as a nanocomposite membrane 18, is disposed in the sample chamber 14. This membrane 18 is in physical contact with the working electrode 6. The sensing chemistry materials preferably include an electron transfer agent, such as a diffusible redox mediator (cannot be shown). The redox mediator and other sensing chemistry materials will be described in detail later. A vent hole 16 is formed in the top layer 12 and the counter electrode 10 through to the sample chamber 14. The substrate 4 and the top layer 12 are recessed such that portions 20, 22 (FIG. 2B) of the working electrode 6 and the counter electrode 10 are left exposed so that they are connectable to an electronic circuit.

The sample chamber 14 is configured or shaped so that when a sample or analyte is provided in the chamber 14, the analyte is in electrolytic contact with both the working electrode 6 and the counter electrode 10. This electrolytic contact allows an electrical current, mediated by the redox mediator, to flow between the electrodes 6, 10 to effect electrolysis (electrooxidation or electroreduction) of the analyte. The redox mediator enables electrochemical analysis of molecules of the analyte which may not be suited for direct electrochemical reaction on the working electrode 6. The volume of the sample chamber 14 can be between 0.1-1 μl, although other volumes are also possible. A region of the sample chamber 14, referred to as a measurement zone, contains only the portion of the analyte that is interrogated during the analyte assay. In the biosensor 2 in FIG. 1, the measurement zone has a volume that is approximately equal to the volume of the sample chamber 14. However, it should be noted that a smaller measurement zone, such as 80% or 90% of the size of the sample chamber 14 is also possible.

The height of the sample chamber 14, as defined by the thickness of spacer 8 is preferably small to promote rapid electrolysis of the analyte, as more of the analyte will be in contact with surfaces of the electrodes 6, 10 for a given analyte volume. In addition, a sample chamber 14 of a small height helps to reduce errors from diffusion of analyte into a smaller-sized measurement zone from other portions of the sample chamber 14 during the analyte assay, because diffusion time is long relative to the measurement time. Typically, the thickness of the sample chamber is no more than about 0.2 mm. Preferably, the thickness of the sample chamber is no more than about 0.1 mm and, more preferably, the thickness of the sample chamber is about 0.05 mm or less.

The substrate 4 and the top layer 12 may be formed from an inert non-conducting material, such as polyester. Alternatively, the substrate 4 and the top layer 12 may be formed from a molded carbon fiber composite. The working electrode 6 preferable has a relatively low electrical resistance and is typically electrochemically inert over the potential range of the biosensor during operation. Suitable materials for forming the working electrode 6 include gold, carbon, platinum, ruthenium dioxide, palladium, and conductive epoxies, such as, for example, ECCOCOAT CT50793 Carbon-Filled Conductive Epoxy Coating (available from W.R. Grace Company, Woburn, Mass.), as well as other non-corroding materials known to those skilled in the art. The counter electrode 10 may also be formed using any of these materials suitable for forming the working electrode 6. The working electrode 6 and the counter electrode 10 may be deposited on the surfaces of the substrate 4 and the top layer 12 by any suitable methods, for example by vapor deposition or printing.

The spacer 8 is typically constructed from an inert nonconducting material such as pressure-sensitive adhesive, polyester, Mylar®, Keviar°, or any other strong, thin polymer film, or, alternatively, a thin polymer film such as a Teflon® film, chosen for its chemical inertness. Other spacers include layers of adhesive and double-sided adhesive tape (e.g., a carrier film with adhesive on opposing sides of the film).

In one specific embodiment, the substrate 4 and the top layer 12 are polyester films, the working electrode 6 is a screen-printed carbon layer, the counter electrode 10 is a screen-printed Ag/AgCl layer and the spacer 8 is a double-sided adhesive tape.

During use of the biosensor 2, the exposed side of the sample chamber 14 is used to contact an analyte, such as blood or a serum. The sample chamber 14, with the nanocomposite membrane 18 therein, receives the analyte for analysis thereof by wicking or capillary action. Depending on the type of redox mediator, the diffusible redox mediator may diffuse rapidly into the analyte or diffusion may occur over a period of time. Similarly, the diffusible redox mediator in the membrane 18 may first dissolve and then diffuse into the analyte, either rapidly or over a period of time. If the redox mediator diffuse over a period of time, a user may be Instructed to wait a period of time before measuring the analyte concentration to allow for diffusion of the redox mediator.

It should not to be construed that the structure and construction of a biosensor is limited to that described above; biosensors having other structures and constructed using other processes are also possible. FIG. 2 shows one such biosensor 24 according to another embodiment of the invention. This biosensor 24, which is a variant of the biosensor 2 in FIG. 1, includes the layers 4, 6, 10, 12 and the membrane 18 of the biosensor 2. However, the spacer 8 in this embodiment includes a first spacer portion 8A and a second spacer portion BB separated by a gap 26 therebetween. This gap 26 defines a sample chamber 14 when the spacer 8 is sandwiched between the working electrode 6 and the counter electrode 10. Two opposing sides of the sample chamber 14 are exposed. Therefore, no vent hole is necessary in the biosensor 20.

Some other biosensors are disclosed in U.S. Pat. No. 6,338,790, Feldman et al., entitled "Small Volume in vitro analyte sensor with diffusible or non-leachable redox mediator." Some of these biosensors include more than one counter electrode 6.

A large variety of oxidoreductases can be employed in a sensor of the present invention. One function of the enzymes in a sensor is to catalyse the oxidation or reduction of the enzyme substrate by the removal or addition of electrons. For example, where the substrate or analyte to be detected is glucose, glucose oxidase may be used to oxidize glucose into gluconic acid. Although it may be thermodynamically feasible for the oxidation of glucose to proceed in the absence of an enzyme, the presence of a suitable oxidoreductase helps to accelerate the oxidation reaction, thereby allowing enzyme activity and substrate analysis to be easily studied. Besides, such enzymes can be obtained cheaply and readily.

In some embodiments of the invention, the oxidoreductase is selected from the group consisting of glucose oxidase, hydrogen peroxidase, horseradish peroxidase, xanthine oxidase, cholesterol oxidase, hydrogen hydrogenase, lactate dehydrogenase, glucose dehydrogenase and NADH dehydrogenase, sarcosine oxidase, lactate oxidase, alcohol dehydrogenase, hydroxybutyrate dehydrogenase, glycerol dehydrogenase, sorbitol dehydrogenase, malate dehydrogenase, galactose dehydrogenase, malate oxidase, galactose oxidase, xanthine dehydrogenase, alcohol oxidase, choline oxidase, xanthine oxidase, choline dehydrohenase, pyruvate dehydrogenase, pyruvate oxidase, oxalate oxidase, bilirubin oxidase, glutamate dehydrogenase, glutamate oxidase, amine oxidase, NADPH oxidase, urate oxidase, cytochrome C oxidase, actechol oxidase and mixtures thereof.

Three commonly used conventions for the labeling of groups in the Periodic Table are, namely, the new IUPAC convention, the old IUPAC convention, (also known as the European convention), as well as the CAS group labeling convention (also known as the American convention). The CAS convention is used in the present application. In the CAS convention, Groups IA, IIA, IIIA and IVA refer to the main group elements of Group 1 (Li, Na, K, etc.), 2 (Be, Mg, Ca, etc.), 3 (B, Al, Ga, etc.) and 4 (C, Si, Ge, etc.), respectively, while Groups IB, IIB, IIIB, IVAB, VB, VIIB, VIIB and VIIIB refer to the transition elements. Groups IA, IIA, IIIA and IVA under the CAS convention are equivalent to Groups IA, IIA, IIIB, and IVB, respectively, under the old IUPAC convention, and equivalent to Groups 1, 2, 13, and 14, respectively, under the new IUPAC convention. Groups IB, IIB, IIIB, IVAB, VB, VIIB, VIIB and VIIIB under the CAS convention are equivalent to Groups IA, IIA, IIIA, IVA, VA, VIA, VIIA and VIIIA, respectively, under the old IUPAC convention, and equivalent to Groups 3, 4, 5, 6, 7, 8-10, 11, and 12, respectively, under the new IUPAC convention.

Nanoparticles that can be used can be any inorganic oxide of an element selected from Group IA, IIA, IIIA, IVA, IB, IIB, IIIB, IVAB, VB, VIIB, VIIB or VIIIB of the Periodic Table. The nanoparticle may have any suitable dimension and shape, as long as they are able to provide an efficient diffusional pathway for the glucose molecules to be transported into the membrane to a location near to the surface of the oxidizing electrode. Furthermore, nanoparticles used in the Invention can be porous or non-porous. The average size of the Inorganic nanoparticles used in the membrane of the Invention typically ranges from about 5 nm to about 1 μm, or from about 100 to about 1000 nm, including from about 100 to about 500 nanometers, or about 200 to about 300 nanometers. The size of nanoparticles can be selected according to the intended application (for example, to influence the length of the diffusional pathway as mentioned above), or also to alter the viscosity or density of the slurry ink that is used for the preparation of the membrane of the invention.

Examples of oxides that are suitable for use in the membrane of the invention include, but are not limited to, lithium manganese oxide, magnesium oxide, zinc oxide, cobalt oxide, yttrium oxide, niobium oxide, calcium oxide, lanthanum oxide, cerium oxide, aluminum oxide, silicon dioxide and mixtures thereof.

In some embodiments, the membrane incorporates nanoparticles of aluminum, silicon, magnesium or zinc oxide(s). The present inventors found that incorporation of such oxides e.g. alumina or silica into the membrane facilitates the preparation of membranes as well as impart good mechanical strength to the membrane, such that it does not crack, even after long periods of use.

With respect to silica particles, any suitable kind of silica particles (for example, fumed silica or colloidal silica) can be used in the invention. Silica particles as every other particles of an inorganic oxide as defined herein can be selected based on a variety of factors, such as its diameter, aspect ratio, average pore size, or shape. These parameters can be chosen for achieving a desired transport characteristic in the nanoparticulate membrane. The choice of suitable particles can also be dependent on the choice of deposition technique. The silica particles may have a size from 5 to about 000 nanometers (nm), or from about 100 to about 1000 nm, including from about 100 to about 500 nanometers, or about 200 to about 300 nanometers. Silica particles can be synthesized in the laboratory or obtained from commercial suppliers. Colloidal silica for example (Chemical Abstracts Number 7631-869) is commercially available from many suppliers. For example, it is sold under the trade name Snowtex® from Nissan Chemicals or under the trade name NYACOL® from Nyacol Nanotechnologies, Inc.

The thickness of the nanoparticulate membrane of the invention ranges from 50 to 1000 micrometers (μm), or from 100 to 700 μm, or preferably from 250 to 500 μm. The thickness of the membrane may depend on several factors such as desired electrode size, or the constituents of the membrane, for example. It may be controlled by the choice of the deposition technique (screen printing, dip coating or spin coating to name a few), the content of the nanoparticulate material or the concentration of the ink slurry. In case screen printing is used for deposition of the ink slurry from which the membrane is made, the thickness of the membrane can be controlled inter alia via the mesh size of the screen.

In yet another embodiment of the sensor, the nanoparticulate membrane of the invention can further comprise a polymeric binder. Any suitable polymeric binder can be used in the membrane, including electrostatically Inert polymers, ionic polymers, polymers capable of acquiring a net charge, polymers capable of providing biconjugation, and proteins. Polyurethane, cellulose or elastomeric polymers are examples of polymers which are electrostatically inert. Examples of polymers that are capable of acquiring a net charge, thereby becoming either positively or negatively charged, are nitrogen-containing heterocycles such as pyridine or imidazole. Glycoproteins are a class of proteins useful in the present application. Specific examples include avidin, blotin and streptavidin, which can conjugate with electrochemical activators present in the membrane to form a suitable polymeric binder for use in the present invention. Useful binders as well as methods for their synthesis are described in U.S. Pat. No. 6,592,745, for example.

In one embodiment, the polymeric binder is a polymer or copolymer comprising monomer units selected from the group consisting of vinyl pyridine, vinyl imidazole, acrylamide, acrylonitrile and acrylhydrazide and acrylic acid monomer units. A specific example of a polymeric binder having monomers selected the group is vinyl pyridine. A binder derived from these monomeric units are suited for glucose sensing applications involving blood samples for example because of its dual function of binding and analyte regulating in the membrane. By incorporating a binder such as vinyl-pyridine into the membrane, the membrane does not break up on hydration, but swells to form a gelled layer holding up the various components of the membrane on the screen-printed carbon surface. Mediators, enzymes and analytes such as glucose can then move freely within this layer, whereas interfering species, such as red blood cells containing oxygenated hemoglobin are excluded from entering the membrane due to electro static repulsion. Anionic ascorbic acid and uric acid are expelled by the anionic binder, and the partition of dissolved oxygen into the nanoparticulate membrane is largely minimized owing to the highly hydrophilic nature of this layer.

The invention is also directed to a process for producing a non-conductive, nanoparticulate membrane. The preparation of a nanocomposite, slurry ink comprising an electrochemical activator such as a redox polymer, an enzyme and nanoparticles can be carried out in a commercially available mixer, blender or stirrer, depending on the quantity, viscosity and homogeneity of the slurry. The slurry can be prepared in any suitable liquid or dispersion medium, for example, polar solvents, aqueous solutions, PBS buffer, and organic compounds or solvents (e.g. alcohol) which can facilitate the processing of the nanoparticulate membrane.

Suitable proportions of components which are used to form the slurry ink vary. For example, the composition may be varied according to the application, or on the enzyme used, or the deposition technique that is employed for depositing the slurry ink and the amounts used for each component can be determined empirically. For example a suitable composition for a slurry ink that is used in the manufacture of a membrane of a glucose sensor may comprise the components in the following range—glucose oxidase: 0.10-1.0 mg/ml; redox mediator 5-50 mg/ml; nanoparticles: 10-200 mg/ml; binder: 10-300 mg/ml. In this example, no standing period is required, but the slurry ink can be used immediately. However, for other preparation the slurry ink may have to stand for a suitable period of time before being applied onto a suitable substrate. In another specific example, the slurry ink may comprise glucose oxidase, poly(VFcAA), alumina nanoparticles and PVPAC binder, mixed with a mixing ratio ranging from 1:50:150:200 to 1:40:200:300 weight parts. A redox polymer of the invention is added to the mixer where it is homogenized with the enzyme, nanoparticles and water. Thereafter, the homogenized mixture is applied on any suitable substrate. A variety of deposition techniques can be employed to deposit the membrane onto a surface, including, but not limited to, spraying, painting, dip coating, spin coating, inkjet printing and screen printing.

As mentioned above, the concentration of a redox mediator in the slurry ink may vary, for example, from 5 to 50 mg/ml. In one example described below where a vinylferrocene-co-acrylamide redox mediator was employed, 10 to 20 mg/ml of the mediator was added to the slurry ink. In one embodiment, the concentration of the redox mediator in the nanocomposite ink is about 15 mg/ml.

The concentration of enzyme in the slurry ink may also vary. A typical range is from 0.1 to 1 mg/ml. In one embodiment, the concentration of enzyme in the nanocomposite ink is about 0.2 mg/ml.

The formulation of the nanocomposite ink can be varied as follows. Since the catalytic reaction occurs between the mediator and enzyme, the concentration of the mediator must be high enough to have a high sensitivity and linear relationship between the catalytic oxidation current and glucose concentration. If the amount of mediator is limited, the amperometric response of the sensor will plateau off even with increasing glucose concentrations in the sample. When this happens, the amount of mediator becomes a bottleneck, and the sensor reading becomes instead dependent on the amount of mediator in the membrane, rather than glucose concentration in the sample. For the specific examples described later, it was found that the optimized mediator concentration was about 15 mg/ml and the optimal concentration of GOX was about 0.20 mg/ml.

The invention also relates to new ferrocene based redox polymers that are amongst other uses well suited for being used as electrochemical activator in glucose sensors of the invention as well as in any as well as any other known electrochemical detection of analytes, for example. Although ferrocene-containing monomers usually undergo free radical polymerization with great difficulty, the inventors have found that redox polymers containing ferrocene can be elegantly and readily prepared using an alcoholic medium prepared from, for Instance, a mixture of ethanol and water, together with a persulfate salt as radical Initiator.

Whilst any organometallic redox species can be used as a redox mediator (e.g. nickelocene and cobaltocene), ferrocene-based redox mediators are preferred, for example due to the suitable redox potential derived from the oxidation of ferrocene to ferrocinium ion.

Ferrocene derivatives can be used as diffusional electron transfer mediators in homogeneous systems. It should be noted that diffusional mediators are typically low in molecular weight and can leach out of the electrode and be lost in the sample that is being measured. For this reason, sensors based on diffusional mediators are suitable as disposable sensors which are used once and disposed immediately thereafter.

Ferrocene derivatives can also be used as mediators that are immobilized on an electrode surface and then attached to a protein molecule, such as an enzyme or an antigen, via crosslinking between crosslinkable functional groups found both in the enzyme and in a side chain of the redox polymer.

Suitable polymerisable ferrocene derivatives that can be used as a first monomer to form a redox polymer should possess a side chain unit having an unsaturated bond, such as a C—C double or triple bond, or a N—N double bond or a S—S double bond. Examples of such side chain units include alkenyl groups, represented by the general formula $R_1$—C=C—. The double bond can be located at any position along the carbon chain. Aromatic groups e.g. phenyl, toluoyl and naphthyl groups can also be used. Furthermore, the polymerisable group can also comprise substituted C-atoms wherein a halogen (e.g. fluorine, chlorine, bromine or iodine), oxygen or hydroxyl moiety for example, substitutes one or more hydrogen atoms on carbon atoms in the group. Further examples include an alkynyl and a disulphide group.

In a preferred embodiment, the polymerisable ferrocene derivative is selected from the group consisting of vinyl-ferrocene, acetylene-ferrocene, styrene-ferrocene and ethylene oxide-ferrocene.

The presence of an unsaturated bond in these derivatives would allow the ferrocene molecule to be attached to a polymer backbone via copolymerisation with another species having also at least one unsaturated C—C double or triple bond, or a N—N double bond or a S—S double bond, via free radical polymerization.

For the second monomer unit that is used in copolymerisation with the polymerisable ferrocene derivative, any suitable acrylic acid derivative having a primary acid or base functional group capable of acquiring a net charge can be used. This means that the invention provides for positively as well as negatively charged polymers and thus ensure that conducting bilayers as explained above can be formed, irrespective of the net charge of the complex formed between capture molecules and analyte molecules. In general, there are two requirements for selecting a suitable acrylic acid derivative for use as a monomer. In order for it to copolymerize with the ferrocene derivative, it should possess of at least one unsaturated bond, which can be provided by a C—C double or triple bond, or a N—N double bond or a S—S double bond for example. Secondly, the acrylic acid derivative should be able to function as a Bronsted-Lowry acid or base by producing $H^+$ Ions or by accepting $H^+$ ions, respectively. Examples of functional groups which can provide a Bronsted-Lowry acid or base function include primary amine groups which can accept $H^+$ ions to form charged amine groups, or carboxyl groups, or sulfate which can donate $H^+$ ions when the acid functionalities dissociates to release $H^+$ ions. In this respect, it is noted that although the use of primary amine groups is preferred in the present application, it is evident for the skilled person that also secondary or tertiary amine groups present in the acrylic acid derivative can be used in order to generate a positively charged redox polymer. In this respect, it is also noted that the acid or base functionality, although it is a primary one, does not need to be a terminal group, but in case of a branched side chain can be present "within" the shorter one of the side chains.

While any suitable acrylic acid derivative having an acid or base functional group can be used, preferred monomers that are used as the second monomer in a redox polymer of the present sensor is an acrylic acid derivative represented by the general formula (I):

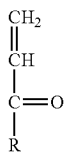

wherein R is selected from the group consisting of $C_nH_{2n}$—$NH_2$, $C_nH_{2n}$—COOH, NH—$C_nH_{2n}$—$SO_3H$, and NH—$C_nH_{2n}$—$PO_3H$, wherein the alkyl chain is optionally substituted, and wherein n is an integer from 0 to 12, preferably 0 to 8. The alkyl group can thus be straight chained or branched, and can also comprise double or triple bonds or a cyclic structure such as cyclohexyl. Examples of suitable aliphatic moieties within the substituent R are methyl, ethyl, propyl, isopropyl, butyl, isobutyl, pentyl, isopentyl, hexyl, cyclohexyl, or octyl to name a few. The aliphatic group can further be substituted by an aromatic group such as phenyl, a halogen atom, a further base or acid group, or an O-alkyl group, for example. Exemplary aromatic groups that can be present as substituents are phenyl, toluoyl or naphthyl. The halogen atom can be selected from fluoride, chloride or bromide. Examples of suitable o-alkyl groups are methoxy, ethoxy, propoxy or butoxy, whereas the n-alkyl group is selected from —NHMe, —N(Me)$_2$, —N(Ethyl)$_2$ or —N(Propyl)$_2$.

The monomer of the acrylic acid derivative, if not commercially available, can be made starting via nucleophilic substitution from acryl amide, for example, by reaction of its terminal $NH_2$-group with an suitable activated derivative of an acid or base compound having an alkyl chain as defined here. For example, acryl amid may be reacted with 4-bromobutanoic acid or a ester derivate thereof, yielding the respective acryl amid monomer. An analogous procedure can be used for the sulfonic or phosphoric acid derivatives.

Typically, for biological samples, the pH can be between about 6.5 to 7.5. Under such a pH range, acrylamide units in the redox polymer can acquire a positive charge i.e. become cationic. This positive charge brings the ferrocene moieties in the polymer, via electrostatic interaction, to a much closer proximity to the redox centers on glucose oxidase (where glucose oxidase is the selected oxidoreductase enzyme) because glucose oxidase is negatively charged, i.e. anionic, in this pH range.

In one sensor of the present invention, the oxidoreductase enzyme is covalently linked to the redox polymer by cross-linkages. The redox polymers of the invention can be co-immobilized with the oxidoreductase enzyme at an electrode surface, making the enzyme an integral (functional) part of the electrode. Coimmobilisation of enzyme and mediator can be achieved by labeling the enzyme with the redox mediator, followed by enzyme immobilization on the electrode surface. Alternatively, the redox polymer can be immobilized on the electrode surface first, and then the enzyme is immobilized in the redox polymer. It is also possible to immobilize both enzyme and redox polymer in a matrix formed from a conducting polymer.

In another sensor of the present invention, the oxidoreductase enzyme and redox polymer are diffusibly dispersed in a nanoparticulate membrane comprising nanoparticles of at least one inorganic oxide of an element selected from Group IA, IIA, IIIA, IVA, IB, IIB, IIIB, IVAB, VB, VIIB, VIIB or VIIIB of the Periodic Table.

In such a sensor, the redox polymers operate as a diffusional mediators shuttling between electrode surfaces and the test sample. A nanoparticulate membrane which incorporates a redox polymer not only provides electron mediating function, but also provides analyte filtering function to prevent electrodes from coming into contact with other electrochemically active materials in the sample. The nanoparticles in the membrane provide microchannels in which analyte molecules can diffuse into in order to reach the oxidizing electrode in the sensor.

In an embodiment of a sensor of the Invention, the redox polymers of formula (I) have a molecular weight of between about 1000 and 5000 Daltons, or preferably between about 2000 and 4000 Daltons.

In another embodiment of the invention, the redox polymer of formula (I) has ferrocene loading between about 2% to 17%, or 3% and 14%. High levels of ferrocene loading, preferably at least above 3%, are desirable. Usually, a low level of ferrocene loading would impose a limit to the glucose concentration that can be measured. For example, where glucose concentration is much higher than the mediating capacity of the ferrocene molecules present, the amperometric response that is generated may be limited by the small number of mediating ferrocene molecules, resulting in an inaccurate measurement. Therefore, by employing the redox polymers of formula (I) having a higher level of ferrocene loading, the upper limit of glucose concentrations that can be tested with the sensor is raised and thus smaller volumes of sample required.

The present invention is also directed to a process for preparing a water soluble, redox polymer. The process essentially involves polymerizing a first monomer unit of a polymerisable ferrocene derivative with a second monomer unit comprising an acrylic acid derivative, such as a primary, secondary or tertiary acrylamide, to produce a copolymer. The acrylic acid derivative possesses an acid or base functional group capable of acquiring a net charge. Importantly, the polymerization reaction is carried out in an aqueous alcoholic medium in the presence of an initiator.

The addition sequence of the monomers and initiator can be varied. For example, it is possible to mix the first and second monomer in alcoholic medium, and then add the initiator to the initiate the reaction. It is also possible to dissolve one of the monomers in aqueous alcoholic medium first, and then add the initiator to it, before adding the other monomer to the mixture.

An alcoholic medium can be prepared with any organic alcohol, for example, aliphatic alcohols such as ethanol, or aromatic alcohols such as phenols. The volumetric ratio is usually within the range of ca 5:1 to 1:1 (alcohol/water). In some embodiments, it is about 3:1.

In an embodiment of the process according to the invention, polymerization is carried out using an aqueous alcoholic solvent comprising ethanol and water in a volumetric ratio of between about 2:1 and 3:1.

Although polymerization may proceed without the addition of an initiator, it is desirable to add a radical initiator which attacks the electron-rich centers found at the unsaturated bonds in the monomers. Accordingly, in another embodiment of the invention, polymerization is initiated by adding a free radical initiator.

Any free radical initiator can be used. Examples include inorganic salts such as persulfate salts, as well as organic compounds such as benzoyl peroxide or 2,2'-azo-bis-isobutyrylnitrile (AIBN), which are able to produce radical fragments called initiator fragments, each of which has one unpaired electron which can function as a free radical which attack the unsaturated bonds in the monomer units.

In some embodiments, the free radical initiator is selected form the group consisting of ammonium persulfate, potassium persulfate and sodium persulfate.

In one embodiment of the invention, the weight ratio of free radical initiator added is between about 20 mg to 40 mg per 1 gram of monomer. The inventors have found that the amount of radical initiator affected the degree of polymerization. High amounts of radical initiator significantly reduced polymerization efficiency, resulting in redox polymers having lower molecular weight. This also meant that relatively little radical initiator was needed in the polymerization process, compared to normal free radical polymerization reactions. Apart from the quantity of free radical initiator used, the addition sequence of reactants (see below in relation to a process of the invention), also affected polymerization efficiency.

The process according to the invention can be carried out at standard conditions of room temperature and pressure. However, in order to accelerate the reaction, it is generally preferred to carry out the reaction mixture under reflux. Care must also be taken not to use an excessively high temperature which might lead to the decomposition of the polymer or the reactants. Thus, a suitable upper limit is generally below 100° C. In a preferred embodiment of the process, polymerization is carried out under reflux at a temperature of between about 60° C. to 80° C.

In a further embodiment, polymerization is carried out under reflux in an inert atmosphere. An inert atmosphere can be provided by nitrogen gas, or helium gas or argon gas for instance.

The length of time that is required for polymerization can be dependent upon the temperature used and the amount of initiator added to the reaction broth. Typically, polymerization is carried out for a period of time between 10 to 40 hours, and preferably for about 24 hours.

One embodiment of the inventive process further comprises a producing a pre-reaction mixture prior to polymerizing said first and second monomers, comprising:
dissolving the acrylic acid derivative monomer unit in an aqueous alcoholic medium, then
adding the free radical initiator, and then
adding the polymerisable ferrocene derivative monomer unit to the mixture.

In a further embodiment of the above process, the feeding ratio of acrylic acid derivative to polymerisable ferrocene derivative in the pre-reaction mixture that falls between about 5% and 15% of the weight of monomer added is preferable in order to obtain a redox polymer having a suitable molecular weight and viscosity.

In yet a further embodiment, the polymerisable ferrocene derivative monomer unit is dissolved in an aqueous alcoholic medium prior to being added to the reaction mixture.

In an embodiment of the process of the invention, the redox polymer is precipitated in an organic solvent. Organic solvents that can be used to dissolve monomers involved in polymerization include ether, ketone and alcohol for example.

EXAMPLES

Example 1

Construction of a Diffusional Mediator Biosensor

FIG. 1 shows an exploded isometric view of a tip-filling biosensor 2 according to an embodiment of the present invention. The manufacturing process of the biosensor 2 according to the specific embodiment is next described. Firstly, an array of carbon electrodes, such as of Electrodag 423SS available from Acheson Colloids Co., Ontario, Calif., U.S.A., is printed using a suitable mask on a polyester-film substrate. The printed substrate is then dried at a temperature of around 70° C. for a predetermined period of time, for example twenty-four hours. Thereafter, a double sided tape with holes appropriately formed therein is placed on the printed substrate. These holes would eventually define the recesses 14 and the openings for exposing the electrode portions 20, 22. A uniformed nanoparticulate membrane is then screen-printed, using a suitable mask, on the working surfaces of the carbon electrodes with an aqueous slurry "ink" of PVFcAA (prepared as described in Example 2, below), GOX, a poly(vinylpyridine-co-acrylic acid) (PVPAC) binder and alumina nanoparticles. The resultant structure is then dried at a temperature of around 37° C. in a controlled environment. The thickness of the nanoparticulate membrane may generally be controlled by adjusting the total content in the ink while keeping a constant volume applied on the working area, and is manipulated for example by adjusting the mesh size of a screen in a screen printer or by adjusting the content of nanoparticulate materials, or the 'concentration' of the printing slurry.

While the above-described structure is being formed, an array of Ag/AgCl or carbon counter electrodes is similarly screen-printed on a second polyester film using a suitable mask and dried. This second polyester film is then positioned over the adhesive tape such that the counter electrodes are aligned with their corresponding working electrodes. Thereafter, the structure is singulated to produce multiple biosensor 2, one of which is shown in FIG. 1.

Example 2

Synthesis of Poly(Vinylferrocene-Co-Acrylamide), Poly(Vinylferrocene-Co-Acrylic Acid) and Poly(Vinylferrocene-O-Acrylamido-Sulphonic Acid) Copolymers Glucose oxidase (GOx, EC 1.1.3.4, from *Aspergillus niger*, 191 units/mg) was purchased from Fluka (CH-9470 Buchs, Switzerland). Ferrocene (Fc), Vinylferrocene (VFc), acrylamide (AA), acrylic acid (AC), 2-acrylamido-2-methyl-1-propane-sulfonic acid (cat. no. 28,273, "acrylamido-sulfonic acid" or AAS) and persulfate salts were purchased from Sigma-Aldrich (St. Luis, Mo., USA.). All other chemicals such as acetone, ethanol, and phosphate buffered saline used were of certified analytical grade. All solutions that were used were prepared with deionized water.

UV spectra of polymers produced in the experiment was performed and recorded on an Agilent 8453 UV-visible spectrophotometer. Molecular weights were determined with a Toyo Soda high performance gel permeation chromatography in water and standard poly(ethylene oxide) and poly(ethylene glycol) for calibration.

i) Synthesis of Poly(Vinylferrocene-Co-Acrylamide) Polymers

Three samples containing 1.0 g acrylamide dissolved in 10 ml of mixture solvent of ethanol/water (3 parts to 1 part) were prepared. A 0.30 ml aliquot of 0.10 g/ml oxygen-free persulfate solution was added to each sample after being deoxygenated for 10 minutes. Three amounts of vinylferrocene ranging from 0.05 g to 0.16 g were dissolved in degassed ethanol to form three vinylferrocene solution samples, the amount of ferrocene that is added for each sample being calculated to obtain acrylamide-to-vinylferrocene feeding ratios (w/w) of 95:5, 90:10 and 85:15, respectively. Each vinylferrocene sample was then added to an acrylamide-Initiator mixture. Reaction mixtures were refluxed at 70° C. for 24 hours in nitrogen atmosphere. After cooling, the reaction mixtures were, separately, added drop-wisely to rapidly stirred acetone in order to precipitate a redox polymer. The precipitated redox polymer was washed with acetone and purified by multiple water-dissolving acetone-precipitating cycles. The purified product was then dried under vacuum at 50° C.

ii) Synthesis of Poly(Vinyl Ferrocene-Co-Acrylic Acid) Polymers

Three samples containing 1.0 g acrylic acid dissolved in 10 ml of mixture solvent of ethanol/water (3 parts to 1 part) were prepared. A 0.30 ml aliquot of 0.10 g/ml oxygen-free persulfate solution was added to each sample after being deoxygenated for 10 minutes. Three amounts of vinylferrocene ranging from 0.05 g to 0.16 g were dissolved in degassed ethanol to form three vinylferrocene solution samples, the amount of vinylferrocene that is added for each sample being calculated to obtain acrylamide-to-vinylferrocene feeding ratios (w/w) of 95:5, 90:10 and 85:15, respectively. Each vinylferrocene sample was then added to an acrylamide-initiator mixture. Reaction mixtures were refluxed at 70° C. for 24 hours in nitrogen atmosphere. After cooling, the reaction mixtures were, separately, added drop-wisely to rapidly stirred acetone in order to precipitate a redox polymer. The precipitated redox polymer was washed with acetone and purified by multiple water-dissolving acetone-precipitating cycles. The purified product was then dried under vacuum at 50° C.

iii) Preparation of Poly(Vinyl Ferrocene-Co-Acrylamido-Sulphonic Acid) Polymers Three samples containing 1.0 g acrylic acid dissolved in 10 ml of mixture solvent of ethanol/water (3 parts to 1 part) were prepared. A 0.30 ml aliquot of 0.10 g/ml oxygen-free persulfate solution was added to each sample after being deoxygenated for 10 minutes. Three amounts of vinylferrocene ranging from 0.05 g to 0.16 g were dissolved in degassed ethanol to form three vinylferrocene solution samples, the amount of vinylferrocene that is added for each sample being calculated to obtain acrylamide-to-vinylferrocene feeding ratios (w/w) of 95:5, 90:10 and 85:15, respectively. Each vinylferrocene sample was then added to an acrylamide-Initiator mixture. Reaction mixtures were refluxed at 70° C. for 24 hours in nitrogen atmosphere. After cooling, the reaction mixtures were, separately, added drop-wisely to rapidly stirred acetone in order to precipitate a redox polymer. The precipitated redox polymer was washed with acetone and purified by multiple water-dissolving acetone-precipitating cycles. The purified product was then dried under vacuum at 50° C.

Results and Discussion

Co-polymerization of vinylferrocene with acrylamide and its derivatives were carried out based on conventional radical polymerization reaction. The general reaction equation is depicted in FIG. 6.

However, in order to successfully co-polymerize the monomers, great attention was given to the terminating effect of vinylferrocene in the system. As mentioned in the introduction section, vinylferrocene usually acts as radical scavenger in the co-polymerization system. It was found that the amount of radical initiator is substantially less that these needed in normal polymerization systems. Higher amounts of radical initiator significantly reduced polymerization efficiency and the molecular weight of the product. Besides, the addition sequence also affects the polymerization efficiency.

Less than 20% of polymerization was observed when adding the persulfate radical initiator to the solution of vinylferrocene and acrylamide. This is probably because the formation of ferrocenium in the reaction mixture which resulted in the retardation of polymerization rate and much early termination of the polymer chain growth process. As shown in Table 1, under optimal conditions, relative high yields were obtained.

TABLE 1

Co-polymerization of vinylferrocene, acrylamide, and its derivatives

| Feeding ratio (w/w) | Yield (%) | VFc content (%) | Molecular weight |
|---|---|---|---|
| AA/VFc 95:5 | 80 | 4% | 3600 |
| AA/VFc 90:10 | 72 | 9% | 3100 |
| AA/VFc 85:15 | 56 | 11% | 2400 |
| AC/VFc 95:5 | 75 | 3% | 2800 |
| AC/VFc 90:10 | 55 | 7% | 2500 |
| AC/VFc 85:15 | 45 | 6% | 2000 |
| AAS/VFc 95:5 | 85 | 6% | 4000 |
| AAS/VFc 90:10 | 75 | 9% | 3500 |
| AAS/VFc 85:15 | 62 | 14% | 3000 |

However, the polymer yields decreased with increasing vinylferrocene feeding ratio, which indicated that the terminating effect in radical polymerization still exists, even though great care has already been taken in the polymerization process. It was also found that minute yields were obtained once the reaction mixture became blue, which was due to the formation of considerable amount of ferrocenium in the polymerization solution. Ferrocene loading varied from 3 to 14%, which is always less than ferrocene content in the monomer feedings.

Ferrocene loading in the redox polymer was determined from elemental analysis. Energy Dispersive X-ray Analysis (EDX) was used for this purpose. The energy of electron beam used on samples of the redox produced is 120 keV. The X-rays generated by the sample was subject to analysis by a lithium drifted silicon detector.

The molecular weight of the redox polymer was determined by gel permeation chromatography. Generally, the redox polymers prepared with higher ferrocene feeding ratio had lower molecular weight and broader molecular weight distribution.

Characterization of the Synthesized Redox Polymers

The synthesized copolymers were light-yellow colored, powdery materials. Molecular weights of the copolymers are in between 2000 and 4000 Daltons. FT-IR experiments (see FIG. 7) clearly showed the complete disappearance of vinyl absorption at 1650 suggesting that both acrylamide and vinylferrocene were successfully polymerized and the resulting redox polymer is of high purity, free of monomers. Further evidence can be found in the 1000-1300 $cm^{-1}$ region. Extremely strong adsorption accompanying by a weak one at 1126 $cm^{-1}$ indicates the presence of ferrocenyl units in the redox polymer and the strong absorption at 1218 $cm^{-1}$ suggested amide groups in the polymer. UV experiments, again, confirmed the successful co-polymerization of vinylferrocene and acrylamide. The minute shoulder at 300 nm is a clear indicative of ferrocene moiety in the co-polymer (see FIG. 8). Having ferrocenyl and amine or carboxylic acid moieties in the redox polymer rendered them with dual-function: redox activity for electron-mediating and chemical activity for crosslinking with proteins.

Increasing the feeding ratio of vinylferrocene was intended to increase the proportion of ferrocenyl moiety within the redox polymer. However, varying the amounts of vinylferrocene also affected the polymer yield. The highest yield obtained was when the vinylferrocene feeding ratio was the lowest, which is in good agreement with the unusual behavior of ferrocenyl compounds in radical polymerization. As indicated in Table 1, although the content of ferrocenyl moiety in the polymer increased with increasing vinylferrocene feeding ratio, but it is by far not linear at all. It was found that, for biosensing purpose, a vinylferrocene feeding ratio of 10% is sufficient, which gives good mediating function and good economy. The amount of initiator used in the polymerization also affected composition and yield of the redox polymer. It was found that good redox polymers were obtained when the initiator is in the range of 20-40 mg per gram of monomers.

Example 3

Obtaining Cyclic Voltammograms of the Redox Polymers

Redox polymers were prepared in phosphate-buffered saline (PBS) solutions in the presence of 0.0 µg GOx, 10 µg GOx, and 10 µg GOx and 10 mM glucose.

Electrochemical tests were performed with an AutoLab potentiostat/galvanostat running under the general purpose electrochemical system (GPES) manager version 4.9. A 3-electrode system cell, housed in a Faraday cage. The electrodes were a (Ag/AgCl) reference electrode, a platinum wire counter electrode and an Au working electrode (surface area of 7.94 $mm^2$).

In contrast to vinylferrocene, the redox polymers that were synthesized have high solubility in water but are insoluble in most organic solvents. This characteristic renders the redox polymers ideal for uses as mediators in biosensing, particularly in enzyme-linked biosensing since most enzymes only work in aqueous media.

FIG. 9 shows typical cyclic voltammograms of the In PBS containing only the redox polymers, the voltammograms exhibited highly reversible solution electrochemistry: the redox waves centered at ~0.18 V (vs. Ag/AgCl), the voltammogram has diffusion-limited shape, the magnitude of the anodic and cathodic peak current is the same, the peak-to-peak potential separation is 60 mV, very close to the theoretical value of 59 mV at 25° C. These redox waves can be assigned to the oxidation and reduction of ferrocenyl moieties in the redox polymers, which indicate excellent redox activity of the polymer. The voltammetric experiments, again, demonstrated that vinylferrocene was successfully co-polymerized with acrylamide and its derivatives and the ferrocenyl moieties in the polymers retain their electroactivities. The redox polymers in PBS are in real solution form with free diffusional behavior. Spiking this solution with varies amounts of glucose did not change the voltammogram at all, which suggests that there is no catalytic oxidation of glucose by the redox polymers alone. Furthermore, no obvious changes were observed when adding small amounts of GOx in the redox polymer solution. The electrochemistry of the resulting solution was practically the same as the redox polymer alone solution. However, when 10 mM glucose was added to this solution, the enzymatic oxidation of glucose by GOx proceeds in the solution. The redox centers in GOx, FAD were converted to $FADH_2$. When the electrode potential was scanned past the redox potential of the redox polymer, significant amount of ferrocene moieties in the redox polymer was oxidized to ferrocenium near the electrode surface. The redox potential of $FAD/FADH_2$ in GOx is −0.36 V (vs. Ag/AgCl), which is much lower than the ferrocene/ferrocenium couple, the ferrocenium moieties in the vicinity of $FADH_2$ oxidize it back to FAD, and the ferrocenium moieties in the redox polymer are reduced to the original ferrocene moieties. These two reactions form a catalytic cycle, as illustrated in FIG. 4, or in other words, glucose oxidation by GOx is mediated by the redox polymer.

Thus, the catalytic reaction by the redox polymer greatly enhances the oxidation current in the solution containing glucose, as seen in FIG. 9 (light grey traces). If the electron-exchange among $FADH_2$, redox polymer and electrode are all very fast, large amount of ferrocenium moieties are produced during electrochemical oxidation, and they are, in turn, rapidly consumed by $FADH_2$. This is the reason for the much lower reduction current of ferrocenium moieties, as compared to that obtained in the glucose-free solution. These data suggests that the redox polymers function effectively as redox mediators in enzymatic reactions, shuttling electrons from the redox centers of enzyme to electrode surface.

Example 4

Synthesis of a Membrane Comprising Vinyl Ferrocene-Co-Acrylamide Cross-Linked with Glucose Oxidase-Bovine Serum Albumin (GOx-BSA)

The cross-linking reaction of the redox polymer with proteins was carried out to study the electrochemical properties of the resulting membrane. The enzyme GOx was used in the present example. Glutaradehyde and poly (ethylene glycol) diglycidyl ether (PEG) were chosen as cross-linkers. Biological grade glutaraldehyde (50% in water, product code 00867-1 EA) and poly (ethylene glycol) diglycidyl ether (PEGDE) (product code 03800) was obtained from Sigma-Aldrich.

First, poly(vinylferrocene-co-acrylamide) obtained from Example 1 was deposited onto a gold electrode. GOx-BSA was modified with the crosslinkers to provide GOx-BSA with an aliphatic carbon chain with a terminal aldehyde functional group which can provide cross linkage with suitable functional groups on the Immobilized mediator. Subsequently, the modified GOx-BSA was deposited and reacted with the immobilized initiator. The aldehyde group on the modified GOx-BSA reacted with the amine group on the PAA-VFc to form a covalent crosslinkages. After reaction was carried out, the PAA-VFc-GOx-BSA film was allowed to dry.

The crosslinked PAA-VFc-GOx-BSA film on gold electrode was subjected to voltammetric analysis. Blank PBS was used, and a potential scan rate of 50 mV/s was applied.

FIG. 10 shows a cyclic voltammogram of the PEG crosslinked PAA-VFc with GOx and BSA on gold electrode In blank PBS. As illustrated in FIG. 10, the cross-linked film exhibited exactly as expected for a highly reversible surface immobilized redox couple (A. J. Bard, L. R. Faulkner, Electrochemical Methods, John Wiley & Sons: New York, 2001.) with little change after exhaustive washing with water and PBS, and after numerous repetitive potential cycling between −0.2 V and +0.8V, revealing a highly stable surface immobilized ferrocenyl film on gold electrode. At slow scan rates, <100 mV/s, a remarkably symmetrical signal was recorded as expected for a surface confined one-electron redox system exhibiting an ideal Nernstian behavior: The peak current is proportional to the potential scan rate, the peak-to-peak potential separation is much less than 59 mV, as observed in the case of diffusional behavior in solution (see FIG. 9), and the width of the current at half-peak height is around 90 mV. Such results ascertain that all of the ferrocenyl redox centers are allowed to reach the electrode surface and proceed to reversible heterogeneous electron transfer. Upon adding 10 mM of glucose to the PBS solution, a typical catalytic electrochemical curve was obtained. However, the reduction peak of the redox polymer disappeared (FIG. 10, light grey trace). This meant that the sensing layer was homogenously maintained in the reduced state by the transfer of electrons from the reduced GOx to the ferrocenyl moieties. The rapid response and current detected indicated excellent mediating function of the redox polymer the high current sensitivity (750 nA/mM glucose) of the biosensors.

Based on these positive results, further examples were carried out to investigate the performance of biosensors incorporating redox polymers of the present invention as a diffusional mediator co-dispersed with glucose oxidase in a nanoparticulate membrane.

Example 5

Preparation of a Nanoparticulate Membrane which Incorporates Co-Dispersed Diffusional Poly(Vinylferrocene-Co-Acrylamide) and Glucose Oxidase I) Preparation of Poly(Vinylferrocene-Co-Acrylamide) Redox Polymer D-(+)-glucose and glucose oxidase (GOX, EC 1.1.3.4, from *Aspergillus niger*, 191 units $mg^{-1}$) were purchased from Sigma-Aldrich (St Louis, Mo., USA). Alumina nanoparticles, with particle size ranging from 10 to 1000 nm, were synthesized in house as follows. Aluminum nitrate (Al$(NO_3)_3$ $9H_2O$, 88.30 g) was dissolved in 471 ml of water, and then added dropwise to a base solution prepared from 205.9 ml of concentrated ammonium hydroxide in 411.93 ml of water. The resulting precipitate was stirred and aged at 25° C. overnight, and then centrifuged for supernatant removal. After washing, drying, and grinding, the precipitate was calcinated at 700° C. in air for 3 hours. The resulting gamma-alumina nanocrystals have a controllable size range between several tens to hundreds of nanometers.

The phosphate-buffer saline solution (PBS) (pH of 7.4) was prepared from phosphate salts (0.020 M) and sodium chloride (0.15 M). The poly(vinylferrocene-co-acrylamide), glucose and GOX solutions were prepared with the PBS buffer. Glucose stock solution was allowed to mutarotate for at least 24 h before use. All solutions were prepared with deionize water obtained from Millipore. All other chemicals used in the present example were of certified analytical grade.

Poly(vinylferrocene-co-acrylamide) (PVFcAA) redox polymer was synthesized according to the following procedure: 0.15 g vinylferrocene and 1.0 g acrylamide were dissolved in 10 ml of aqueous alcohol (2, parts ethanol:1 part water). To initiate polymerization, a 0.50 ml aliquot of 0.10 g/ml oxygen-free ammonium persulfate solution was added to the reaction mixture after 10 minutes of deoxygenating. The mixture was refluxed for 24 h under nitrogen. After cooling, the redox polymer was precipitated in acetone. Purification was performed by dissolving the crude product in water and precipitating in an acetone/water mixture.

II) The Synthesis of Nanocomposite Membrane

The nanocomposite membrane was screen-printed onto carbon strip using an aqueous slurry "ink" of PVFcAA, GOX, a poly(vinylpyridine-co-acrylic acid) (PVPAC) binder and alumina nanoparticles. The aqueous slurry Ink was prepared by mixing PVFcAA as prepared above, GOX, poly(vinylpyridine-co-acrylic acid) (PVPAC) or poly(vinylpyridine-co acrylamo-sulfonic acid (PVPPAS) binder and alumina nanoparticles into water according to the following range of concentrations: Glucose oxidase: 0.20-0.50 mg/ml, mediator 10-20 mg/ml, nanoparticles: 30-100 mg/ml, PVPPAC or PVPPAS Binder: 40-150 mg/ml. The slurry ink can be stored or immediately used. When it is desired to coat a sensor electrode with a membrane layer, the slurry ink is loaded into a deposition apparatus such as a screen printing machine, and deposited onto the electrode to form the membrane. Prior to assembly into a sensor, the membrane is first allowed to dry.

Example 6

Cyclic Voltammetry Analysis of a Glucose Biosensor Using a Diffusional Poly(Vinylferrocene-Co-Acrylamide) Mediator and Glucose Oxidase Co-Dispersed in a Nanoparticulate Membrane A sensor was assembled with a screen printed carbon working electrode and a Ag/AgCL reference electrode in the present example, using a slurry ink as prepared in Example 5. The performance of the sensor was analyzed using cyclic voltammetry. All electrochemical measurements were carried out with a model CHI 660A electrochemical workstation (CH Instruments, Austin, USA) at room temperature. Cyclic voltammetric measurements were performed using a conventional three-electrode system, consisting of a screen-printed carbon working electrode, a miniature Ag/AgCl reference electrode (Cypress Systems, Lawrence, Kans., USA) and a platinum wire counter electrode. To avoid the spreading of the printing ink beyond the 2-mm diameter working area, a patterned hydrophobic film was applied to the carbon electrode. To avoid electrode fouling and possible concentration changes in the ink, fresh electrode and ink were used for each voltammetric test. All glucose measurements were performed in the PBS solution. In experiments where the pH was varied, 1.0 M HCl and 1.0 M NaOH solutions were used to adjust the pH of the PBS buffer. In amperometric experiments, the working electrode was poised at 0.30 V (vs. Ag/AgCl).

Results and Discussion

Figure 12:
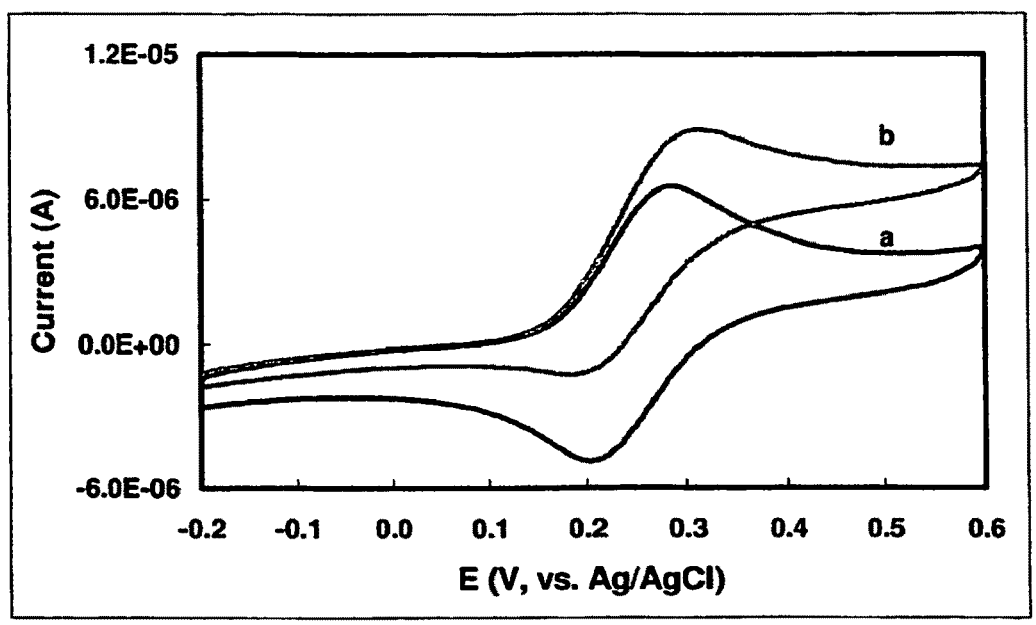
FIG. 12 shows a cyclic voltammograms of the nanoparticulate printing ink (a) without and (b) with the addition of 100 mg/dl glucose. Potential scan rate which was applied was 100 mV/s.

A typical cyclic voltammogram of the PVFcAA mediator in a plain nanocomposite ink is shown in FIG. 12. The electrode exhibited classical features of a diffusion-controlled kinetically fast redox couple. The peak current increased linearly with the square root of potential scan rate, and the difference between the reduction and oxidation peak potential remained unchanged at 59 mV for scan rates up to 200 mV/s, showing that charge transfer from the mediator to the electrode is rapid. Spiking this ink with glucose did not change the voltammogram at all, which suggests that there is no catalytic oxidation of glucose by the mediator alone. Furthermore, practically identical voltammograms, as that shown in FIG. 12a, were obtained in the presence of different amounts of GOX, ranging from 0.10 to 20 mg/ml, indicating that the enzyme does not appreciably affect the electrochemistry of the $Fc^+/Fc$ redox couple in the ink. However, an addition of a very small amount of glucose to this ink resulted in an enhanced anodic current and a diminished cathodic current (FIG. 12b). In addition, as can be seen in FIG. 12b, the voltammogram was lifted up towards the anodic side around the redox potential of the mediator. Such changes are indicative of a typical chemically coupled electrode process (electrocatalysis). The electrocatalysis can be described by the following reaction sequence:

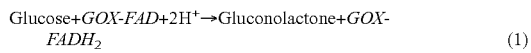

$$\text{Glucose} + GOX\text{-}FAD + 2H^+ \rightarrow \text{Gluconolactone} + GOX\text{-}FADH_2 \quad (1)$$

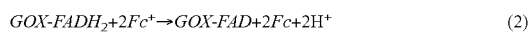

$$GOX\text{-}FADH_2 + 2Fc^+ \rightarrow GOX\text{-}FAD + 2Fc + 2H^+ \quad (2)$$

$$Fc \rightarrow Fc^+ + e^- \quad (3)$$

Thus, the GOX-FAD is reduced to the GOX-FADH$_2$ by the glucose penetrating to the membrane (Eq. 1), electrons are transferred from the GOX-FADH$_2$ to the Fc$^+$ sites (Eq. 2), and the electrons are then transferred through the Fc$^+$/Fc sites of the polymeric mediator to the electrode surface (Eq. 3). The oxidation of ferrocene moieties at the underlying carbon electrode accounts for the enhanced anodic current seen in FIG. 12b.

The rate constant k of the catalytic reaction between Fc and GOX can be estimated from the voltammetric data obtained in the presence of a large excess of glucose to ensure that the enzyme is completely reduced. Under such circumstances, the reaction between GOX and Fc (Eq. 2) is practically pseudo-first-order. As shown by Nicholson and Shain, and Uaudet and co-workers, the limiting current, $I_L$, due to the mediated redox process between Fc and GOX can be described as follows:

$$I_L = nFAC_{Fc}(2D_{Fc}kC_{GOX})^{1/2} \quad (4)$$

where $C_{Fc}$ and $C_{GOX}$ are the concentrations of Fc and GOX, respectively. $D_{Fc}$ is the diffusion coefficient of Fc, and other symbols have their usual meanings. As anticipated from Eq. 4, the limiting current was independent of potential scan rate at sufficiently slow rates, and was proportional to Fc concentration and the square root of GOX concentration. These observations justified the use of Eq. 4 in determining the rate constant of the mediated glucose oxidation. By combining Eq. 4 and the peak current, $i_p$, expression in linear sweep voltammetry, the $I_L/i_p$ relationship is obtained as follows:

$$I_L/i_p = (2kC_{GOD})^{1/2}/[0.4463(nFv/RT)^{1/2}] \quad (5)$$

which contains experimental parameters that are easy to determine and is well-suited for the purpose of determining the rate constant since the electrode process of Fc/Fc$^+$ couple is solely controlled by diffusion. The rate constant was found to be about $3.8 \times 10^3$ l/s mol, estimated from data obtained at slow scan rates, <5.0 mV/s, in solutions containing 0.50 mM Fc, 60 mM glucose and 0-30 µM GOX. Such a rate constant suggests that PVFcAA efficiently mediates the oxidation of GOX and is an excellent mediator for coupling the enzymatic oxidation of glucose to an electrode surface. The rate constant obtained in this work is significantly larger than those of other ferrocene derivative-GOX systems previously reported. A possible cause could be the presence of cationic acrylamide units in the redox polymer at pH 7.4, which brings the Fc moieties to a much closer proximity of the redox centers of GOX via electrostatic interaction since GOX is anionic at this pH.

Example 7

Figure 13:
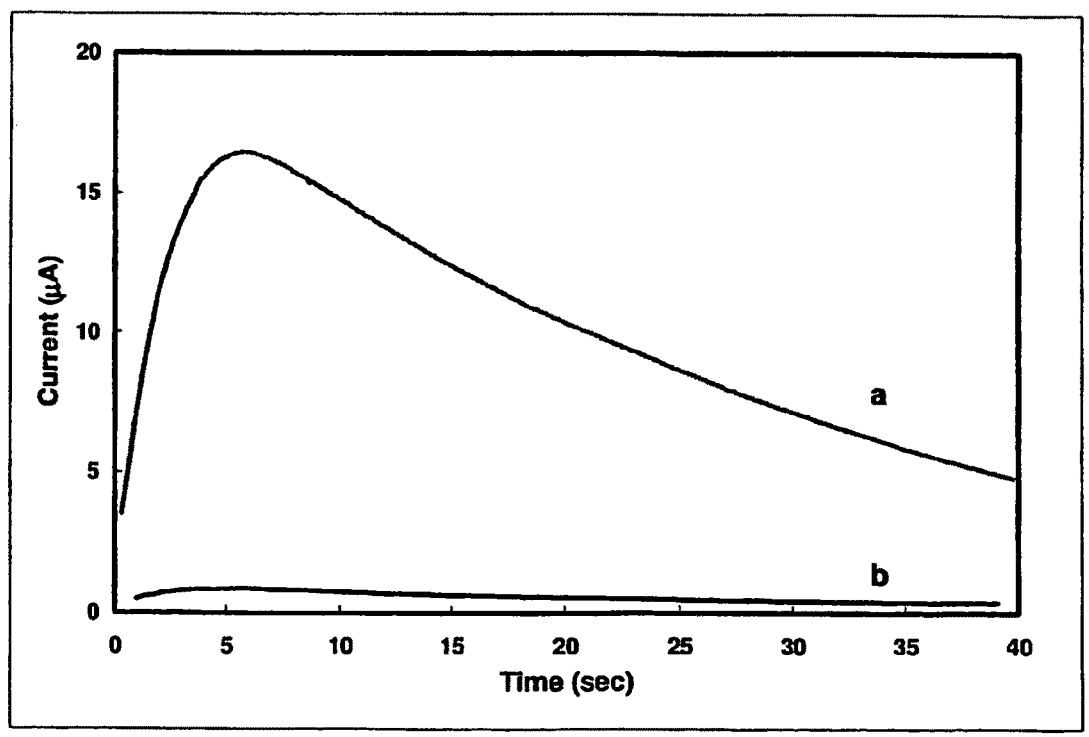
FIG. 13 shows amperometric responses of the biosensor in PBS containing (a) 200 and (b) 0.0 mg/dl glucose. The poised potential applied was 0.30 V.

Amperometric Response of a Glucose Biosensor Using Diffusional Poly(Vinylferrocene-Co-Acrylamide) Mediator and Glucose Oxidase Co-Dispersed in a Nanoparticulate Membrane A sensor was assembled with a screen printed carbon working electrode and a Ag/AgCL reference electrode in the present example, using a slurry ink as prepared in Example 5. A typical amperometric response of glucose in an air-saturated PBS buffer at the biosensor is shown in FIG. 13a. Amperometric tests demonstrated that the biosensor has a rapid response time and high sensitivity to glucose. At 0.30 V, after spiking the glucose concentration, the oxidation current increased and reached the maximum very rapidly, within 5 s, followed by a gradual transient which maintains more than 60% of the peak current for a period of 20 s. No catalytic oxidation current was observed in a blank PBS buffer under identical experimental conditions (FIG. 13b), but the presence of the nanoparticulate membrane did increase the background current and it took a considerably long time to drop to a minute level.

Figure 14:
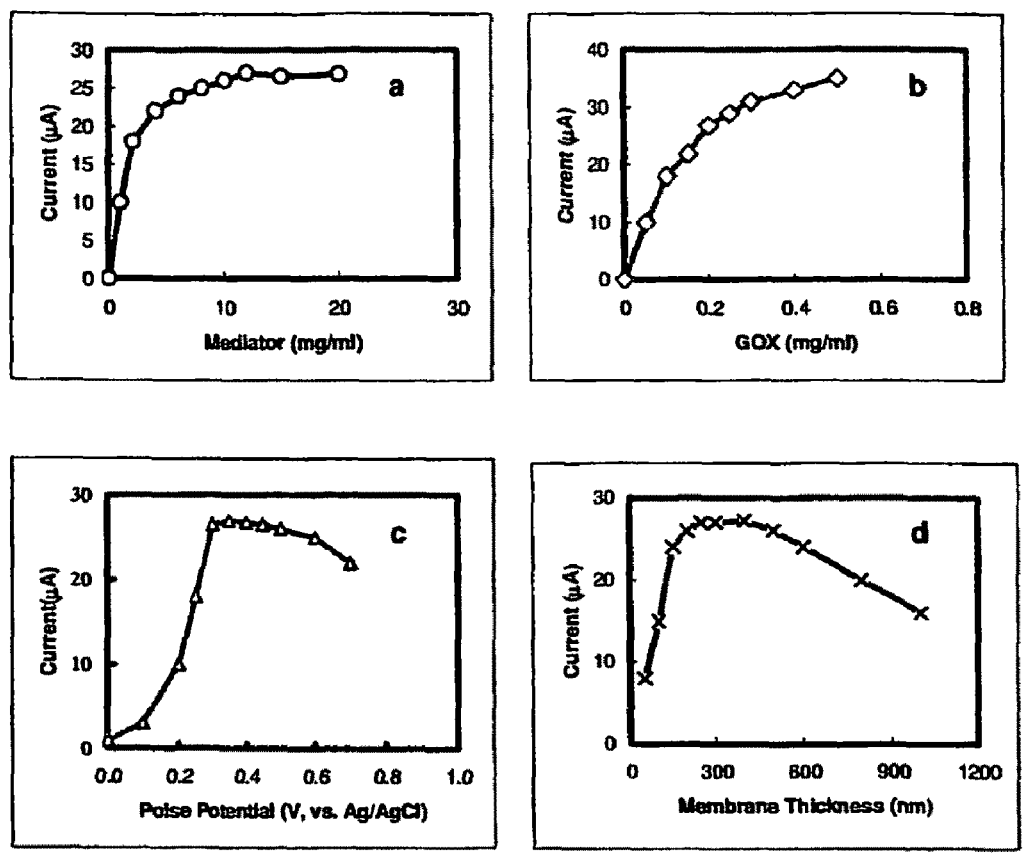
FIG. 14 shows dependence of amperometric peak current of 300 mg/dl glucose on (a) PVFcAA concentration, (b) GOX concentration, (c) poise potential and (d) the nanoparticulate membrane thickness.

In order to obtain a satisfactory performance of the biosensor, the formulation of the nanocomposite ink was optimized. Since the catalytic reaction occurs between the mediator and GOX, the concentration of the mediator must be high enough to have a high sensitivity and linear relationship between the catalytic oxidation current and glucose concentration. Otherwise, the fraction of mediated glucose oxidation will be small and dependent on the amount of mediator in the membrane, instead of the glucose concentration. It was found that a mediator concentration of 15 mg/ml was best for our purpose and the optimal concentration of GOX was found to 0.20 mg/ml, taking into consideration of both sensitivity and biosensor economy (FIGS. 14a and 14b). The poise potential is expected to affect the amperometric response of the biosensor; it was therefore examined in the range of 0.0 to 0.70 V. As illustrated in FIG. 13c, the current sensitivity increased with increasing poise potential and reached a plateau at 0.30 V. A slight decrease in sensitivity was observed when the poise potential became more positive than 0.50 V, presumably due to an increased background current. Moreover, too high a poise potential compromises the accuracy of glucose measurements owing to complications from both the much increased background current and possible direct oxidation of a number of electroactive species at the underlying electrode. For amperometric measurements of glucose, the potential of the biosensor was therefore poised at 0.30 V.

The dependence of the catalytic oxidation current of glucose on the thickness of the nanoparticulate membrane was also investigated (FIG. 14d). As can be seen in FIG. 14d, the catalytic oxidation current reached maximum for nanoparticulate membranes with thicknesses of 250-500 µm. Insufficient materials in thinner membranes resulted in lower sensitivity and the disappearance of the current peak, On the other hand, further increase in membrane thickness beyond 500 µm could inversely affect the membrane permeability for glucose and the oxidation products of the GOX-catalyzed reaction. In addition, longer response times were noted for thicker membranes.

Unlike those utilizing surface-immobilized sensing membrane, the utilization of the non-conductive nanoparticulate sensing membrane offers great advantages over known disposable glucose biosensors in terms of selectivity. In the former systems, the sensing membrane is part of the electrode and is in direct contact with blood samples. Some constituents in blood, such blood cells, both red and white, proteins and ascorbic acid may interact with the sensing membrane and compromise the accuracy of blood sugar measurements. In this work, the nanoparticulate membrane is non-conductive, and therefore structurally and functionally is not part of the electrode. Catalytic oxidation of glucose only takes place at the electrode/nanoparticulate membrane interface. In other words, no electroactive species exchanges electrons with the electrode unless it passes through the nanoparticulate membrane to reach that interface. Thus, the nanoparticulate membrane provides a barrier to the passage of possible interferences of bulky species in blood such as cells and proteins. When this formulation was used to print the nanoparticulate membrane, the PVPAC binder serves a dual function in the sensing membrane: binding and analyte regulating. On rehydration, the membrane does not break up, but swells to form a gelled layer on the screen-printed carbon surface. Reactants, such as glucose and mediators move freely within this layer, whereas interfering species, such as red blood cells containing oxygenated hemoglobin are excluded. Anionic ascorbic acid and uric acid are expelled by the anionic PVAC polymer, and the partition of dissolved oxygen into the nanoparticulate membrane is largely minimized owing to the highly hydrophilic nature of this layer. This resulted in a sensing membrane whereby the amount of current generated in response to a given glucose concentration varied by less than 5.0% over a hematocrit range of 40-60% and in the presence of 0.20 mM ascorbic and 0.10 mM uric acid. Such desirable insensitivity towards the interfering constituents in blood was also observed in whole blood samples. Furthermore, the nanoparticulate membrane presented an analyte regulating layer for glucose too, significantly slowing down the transport of glucose so that the system was not kinetically controlled, thereby extending the linear domain through the entire physiologically relevant glucose concentration range of 40 to 540 mg/dl.

Figure 15:
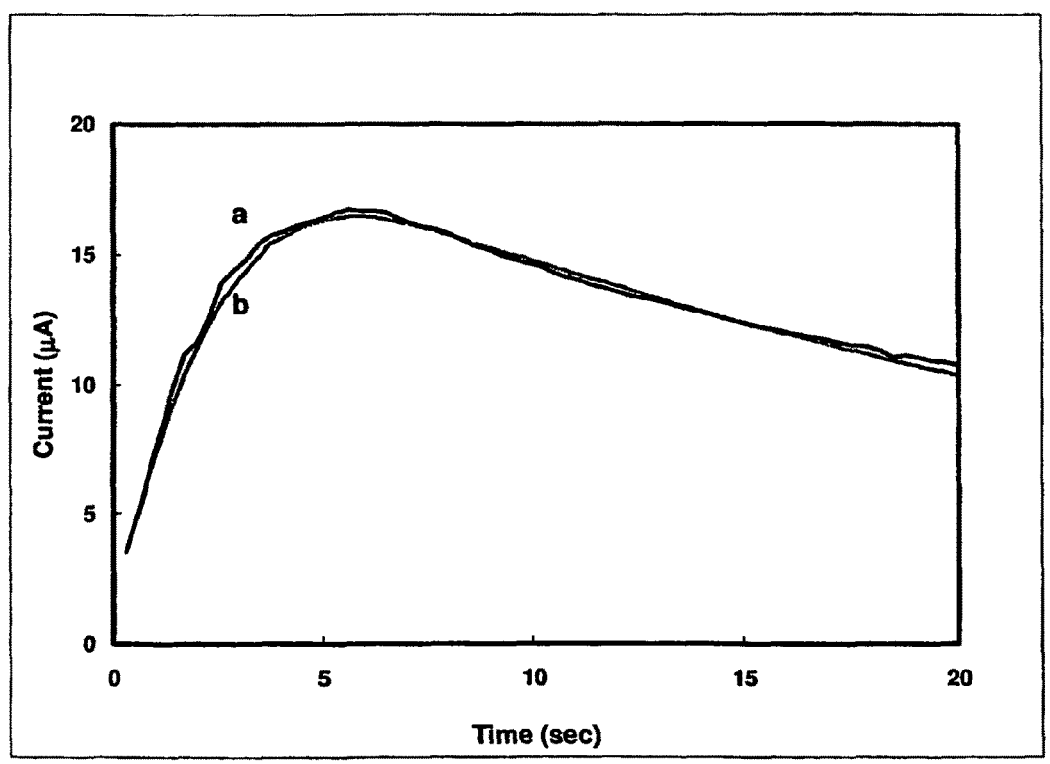
FIG. 15 shows amperometric responses of 200 mg/dl glucose in PBS in the (a) absence and (b) presence of dissolved oxygen. The poised potential applied was 0.30 V.

As mentioned earlier, oxygen affects the sensitivity of the glucose biosensor because glucose oxidation by dissolved oxygen occurs simultaneously as a side-reaction. Initial amperometric tests on thin nanoparticulate membranes employing a hydrophobic polyvinylpyridine (PVP) binder showed that the response was higher in the absence of oxygen than that with dissolved oxygen. At low glucose concentrations, e.g. 50 mg/dl, the competition with oxygen caused a significant decrease (~20%) in peak current. Hence, there was a need to suppress the oxygen interference in the system to achieve a highly selective and accurate biosensor. Introduction of acrylic acid units into the hydrophobic PVP resulted in a marked improvement of the biosensor performance. The resulting nanoparticulate membrane was highly hydrophilic, which improved the glucose/oxygen permeability ratio and optimized the accuracy and linearity of the biosensor response. The two amperometric graphs for 200 mg/dl glucose solutions bubbled with nitrogen (FIG. 15a) and oxygen (FIG. 15b) overlaid nicely with a difference of less than 5% in peak current, showing that the biosensor was rather insensitive to the oxygen content in the samples.

Example 8

Figure 16:
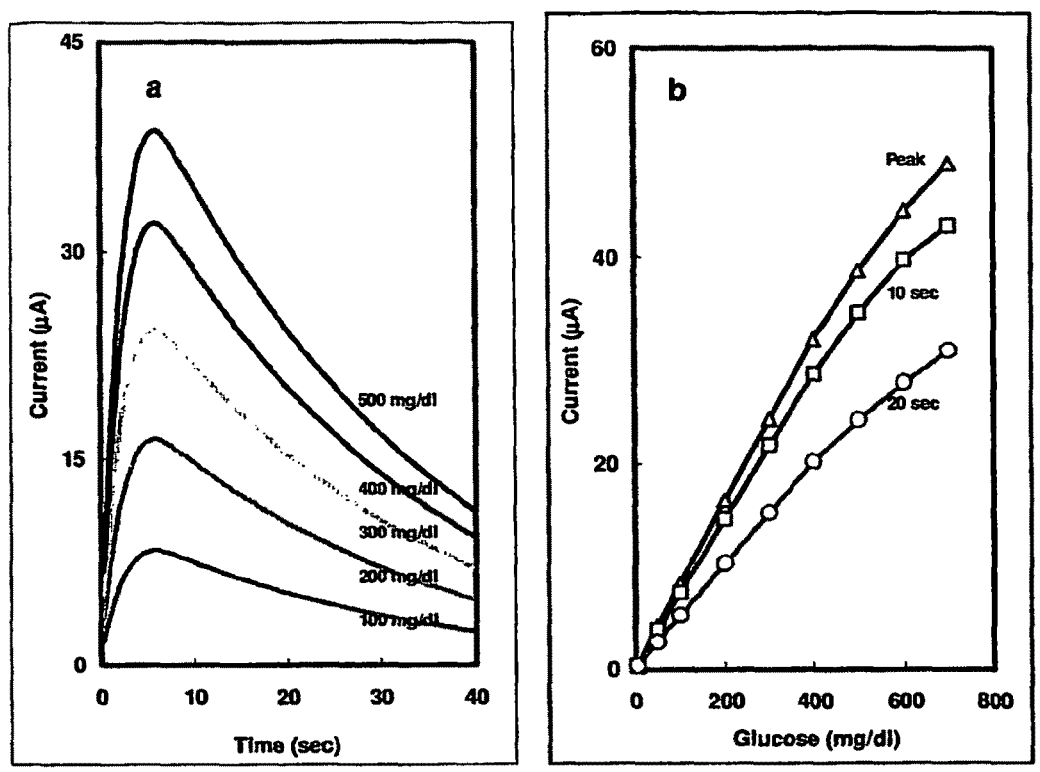
FIG. 16 shows (a) amperometric responses to sequential increases of 100 mg/dl glucose in PBS and (b) calibration curves at different sampling times. The poised potential applied was 0.30 V.

Analysis of Characteristics of a Glucose Biosensor Using a Diffusional Poly(Vinylferroeone-Co-Acrylamide) Mediator and Glucose Oxidase Co-Dispersed in a Nanoparticulate Membrane A sensor was assembled with a screen printed carbon working electrode and a Ag/AgCL reference electrode in the present example, using a slurry ink as prepared in Example 5. The sensitivity was ~76 nA/mg/dl for the peak current for glucose concentrations of $\leqq 600$ mg/dl. As seen in FIG. 16, the catalytic oxidation current was directly proportional to the glucose concentration up to 600 mg/dl, covering the entire physiologically relevant blood sugar levels. Interestingly, currents obtained at any point of time after the current peak was also linearly dependent on the glucose concentration (see FIG. 16b), providing alternative sampling possibilities within the first 20 seconds of the amperometric tests. The precision was estimated from two series of 20 repetitive measurements of 40 and 300 mg/dl glucose solutions. The relative standard deviations were 4.0% and 8.6%, respectively. The detection limit, estimated from 3 times the standard deviation of repetitive measurements of 5.0 mg/dl glucose under optimal conditions, was found to be 1.8 mg/dl, which is limited by the charging current of the biosensor. More importantly, the blood sample volume needed for a single test was about 0.20 to 0.30 μl, the smallest sample volume amongst all the disposable glucose biosensors available on market. The stability tests were carried out at different temperatures. It was shown that the biosensor maintained 100% of its initial sensitivity for the first 180 days of storage at room temperature, lost 10% of its initial sensitivity after 60 min exposure at 50° C. and about 50% of its initial sensitivity after 60 min at 60° C. This may be due to the loss of enzyme activity In the biosensor. The proposed method was successfully applied to the determination of glucose in whole blood (Table 2).

TABLE 2

Results of blood sugar analysis (average of 10 tests)

| Sample | Glucose (mg/dl) | Reference Value (mg/dl)* | Recovery (%) (+50 mg/dl glucose) |
|---|---|---|---|
| Whole Blood 1 (Healthy person) | 80 | 84 | 96.3 |
| Whole Blood 2 (Healthy person) | 110 | 115 | 99.2 |
| Whole Blood 3 (Healthy person) | 105 | 105 | 104 |
| Whole Blood 4 (Diabetic patient) | 185 | 179 | 98.5 |
| Whole Blood 5 (Diabetic patient) | 155 | 158 | 97.1 |

*Obtained with the YSI blood sugar analyzer.

The results obtained were in good agreement with the reference values obtained with a yellow springs blood sugar analyzer (YSI Model 2300). The recoveries obtained were also good enough for practical use.

A series of water-soluble and cross-linkable ferrocenyl redox polymers have been prepared by conventional radical polymerization of vinylferrocene and acrylamide and its derivatives. The resulting redox polymers produced a typical catalytic oxidation current for glucose in the presence of GOx. The experimental results showed that the redox polymers retained their fast electron transfer properties and the GOx retained its catalytic activity after they were introduced in PBS. The redox polymers having amine or carboxylic acid moiety as one of the side chains allow them to be conveniently cross-linked with proteins, such as enzymes and antibodies and antigens. Electrochemical tests of the cross-linked redox polymer films showed excellent catalytic activity towards the oxidation of substrate in solution, high sensitivity, good reproducibility and stability, thus Indicating that it is suitable to be used as sensing membrane in biosensors.

In separate experiments, it was also shown that glucose oxidase and PVFcAA can be readily and homogeneously dispersed into the nanoparticulate alumina together with the hydrophilic PVPAA binder, and the resulting membrane produced a typical catalytic oxidation current for glucose. The experimental results showed that the mediator retained its fast electron transfer properties and the GOX retained its catalytic activity after they were screen-printed onto the carbon electrode. they also demonstrated that this biosensor has good sensitivity and stability for blood sugar monitoring with a blood sample volume of as little as 0.20 μl. The use of screen-printing techniques in the fabrication of the biosensor enables easy and low-cost mass production. These biosensor characteristics are promising for development of miniature glucose biosensors of high commercial values.

What is claimed is:

1. A method for on-line monitoring of test sensors using x-ray fluorescence (XRF) spectrometry, the method comprising:
    providing a test sensor comprising a reagent, the reagent including an enzyme and a mediator, the mediator including metal;
    monitoring an amount of metal in the mediator of the reagent of the test sensor using XRF spectrometry; and
    determining from the amount of metal an amount of the reagent on the test sensor.

2. The method of claim 1, wherein the mediator is a ferricyanide derivative and wherein the monitoring of the amount of metal in the mediator includes measuring the iron.

3. The method of claim 2, wherein the ferricyanide derivative is potassium ferricyanide.

4. The method of claim 1, wherein the mediator is a ferrocene derivative.

5. The method of claim 4, wherein the ferrocene derivative is 1,1' dimethylferrocene, hydroxymethylferrocene, 2-hydroxyethylferrocene or carboxylateferrocene.

6. The method of claim 1, wherein the mediator is ruthenium hexaamine.

7. The method of claim 6, wherein the enzyme is a glucose oxidase.

8. The method of claim 1, wherein the enzyme is a glucose-specific enzyme.

9. The method of claim 1, wherein the metal comprises at least two metallic elements.

10. A method for on-line monitoring of electrochemical test sensors using x-ray fluorescence (XRF) spectrometry, the method comprising:
    providing an electrochemical test sensor comprising a reagent printed thereon, the reagent including an enzyme and a mediator, the mediator including metal; and
    monitoring an amount of metal in the mediator of the reagent of the test sensor using XRF spectrometry; and
    determining from the amount of metal an amount of the reagent on the test sensor.

11. The method of claim 10, wherein the mediator is a ferricyanide derivative and wherein the monitoring of the amount of metal in the mediator of the reagent of the test sensor includes measuring the iron.

12. The method of claim 10, wherein the ferricyanide derivative is potassium ferricyanide.

13. The method of claim 10, wherein the mediator is a ferrocene derivative.

14. The method of claim 13, wherein the ferrocene derivative is 1,1' dimethylferrocene, hydroxymethylferrocene, 2-hydroxyethylferrocene or carboxylateferrocene.

15. The method of claim 10, wherein the mediator is ruthenium hexaamine.

16. The method of claim 10, wherein the enzyme is a glucose-specific enzyme.

17. The method of claim 16, wherein the enzyme is a glucose oxidase.

18. A method of maintaining consistency in the printing of reagents on test sensors comprising:
    providing a test sensor comprising a reagent printed thereon, the reagent including an enzyme and a mediator, the mediator including metal; and
    measuring an amount of metal in the mediator of the reagent of the test sensor wherein the measuring comprises scanning a region of the test sensor with an x-ray fluorescence (XRF) spectrometer; and determining from the measurement of the amount of metal an amount of the reagent printed on the electrochemical test sensor.

19. The method of claim 18, further comprising repeating the providing, measuring, and determining for a number of sample test sensors of the set of test sensors.

20. The method of claim 19, further comprising evaluating the consistency of the printing of the reagent on the test sensors from the determinations of the amounts of the reagents of the sample test sensors.

21. A method for on-line monitoring using x-ray fluorescence (XRF) spectrometry, the method comprising: providing a substrate comprising an organic compound printed thereon, the organic compound including metal; monitoring an amount of the metal in the organic compound on the substrate using XRF spectrometry; and determining from the amount of metal an amount of the organic compound printed on the substrate.

22. The method of claim 21, wherein the organic compound is a reagent including an enzyme and a mediator, and wherein the mediator comprises the metal.

23. The method of claim 21, wherein the substrate comprises a test sensor.

* * * * *